United States Patent
Herr et al.

(10) Patent No.: US 8,921,123 B2
(45) Date of Patent: *Dec. 30, 2014

(54) MULTI-DIRECTIONAL MICROFLUIDIC DEVICES COMPRISING A PAN-CAPTURE BINDING REGION

(75) Inventors: Amy E. Herr, Oakland, CA (US); Dohyun Kim, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/303,047

(22) Filed: Nov. 22, 2011

(65) Prior Publication Data

US 2012/0135541 A1    May 31, 2012

Related U.S. Application Data

(60) Provisional application No. 61/416,693, filed on Nov. 23, 2010.

(51) Int. Cl.
*G01N 33/561* (2006.01)
*G01N 27/447* (2006.01)
*B01L 3/00* (2006.01)
*G01N 33/68* (2006.01)

(52) U.S. Cl.
CPC ..... *G01N 33/6803* (2013.01); *B01L 2400/0415* (2013.01); *B01L 2200/0652* (2013.01); *G01N 27/44791* (2013.01); *B01L 3/50273* (2013.01); *G01N 2550/00* (2013.01); *B01L 2300/0816* (2013.01); *B01L 2300/0864* (2013.01); *B01L 2300/0636* (2013.01); *B01L 2400/0672* (2013.01); *B01L 2400/0406* (2013.01); *B01L 2300/0819* (2013.01); *B01L 2300/0867* (2013.01); *B01L 3/502707* (2013.01); *B01L 3/502753* (2013.01); *B01L 3/502715* (2013.01); *B01L 2400/0421* (2013.01)
USPC ............ 436/516; 436/514; 436/515; 436/518

(58) Field of Classification Search
USPC .......................................... 436/514–516, 518
See application file for complete search history.

(56) References Cited

U.S. PATENT DOCUMENTS 5,407,546 A * 4/1995 Schickle ........................ 204/459
5,420,016 A * 5/1995 Boguslaski et al. ............. 435/12
(Continued)

FOREIGN PATENT DOCUMENTS

JP    2004-61319 A    2/2004
JP    2006-10529 A    1/2006
(Continued)

OTHER PUBLICATIONS

Subramanian, Dye-ligand affinity chromatography: the interaction of cibacron blue F3Ga with proteins and enzymes, 1984, Critical Reviews in Biochemistry and Molecular Biology, 16(2): pp. 169-205.*

(Continued)

*Primary Examiner* — Melanie Y Brown
(74) *Attorney, Agent, or Firm* — Bret E. Field; Bozicevic, Field & Francis LLP

(57) ABSTRACT

Microfluidic devices and methods for using the same are provided. Aspects of the invention include microfluidic devices that include a separation medium and a pan-capture binding medium. The microfluidic devices are configured to subject a sample to two or more directionally distinct electric fields. Also provided are methods of using the devices as well as systems and kits that include the devices. The devices, systems and methods find use in a variety of different applications, including diagnostic and validation assays.

32 Claims, 20 Drawing Sheets

(56) References Cited

U.S. PATENT DOCUMENTS

| | | | |
|---|---|---|---|
| 5,637,469 | A | 6/1997 | Wilding et al. |
| 5,858,195 | A * | 1/1999 | Ramsey .................. 204/601 |
| 6,499,499 | B2 | 12/2002 | Dantsker et al. |
| 6,613,581 | B1 | 9/2003 | Wada et al. |
| 6,818,112 | B2 | 11/2004 | Schneider et al. |
| 6,969,452 | B2 | 11/2005 | He et al. |
| 6,974,526 | B2 | 12/2005 | Lee et al. |
| 7,112,444 | B2 | 9/2006 | Beebe et al. |
| 7,235,389 | B2 | 6/2007 | Lim et al. |
| 7,241,421 | B2 | 7/2007 | Webster et al. |
| 7,641,780 | B2 | 1/2010 | Lee et al. |
| 7,754,150 | B2 | 7/2010 | Wada et al. |
| 8,329,016 | B1 * | 12/2012 | Sommer et al. ............ 204/605 |
| 2001/0041332 | A1 * | 11/2001 | Hillebrand et al. ............ 435/6 |
| 2002/0153046 | A1 | 10/2002 | Dantsker et al. |
| 2003/0089605 | A1 | 5/2003 | Timperman |
| 2003/0127331 | A1 * | 7/2003 | Leka ........................ 204/466 |
| 2004/0112751 | A1 | 6/2004 | Han et al. |
| 2004/0158890 | A1 * | 8/2004 | Thomashow et al. ........ 800/279 |
| 2004/0209354 | A1 | 10/2004 | Mathies et al. |
| 2005/0020814 | A1 | 1/2005 | Rudolph et al. |
| 2005/0106740 | A1 * | 5/2005 | Boyes et al. ................ 436/86 |
| 2005/0155861 | A1 | 7/2005 | Guzman et al. |
| 2005/0217996 | A1 | 10/2005 | Liu et al. |
| 2005/0269267 | A1 | 12/2005 | Patton et al. |
| 2006/0191792 | A1 * | 8/2006 | Herr et al. ................ 204/455 |
| 2007/0121111 | A1 * | 5/2007 | Blumenfeld et al. ........ 356/318 |
| 2009/0071828 | A1 | 3/2009 | Squires et al. |
| 2009/0194483 | A1 | 8/2009 | Robotti et al. |
| 2010/0108519 | A1 * | 5/2010 | Soper et al. ................ 204/601 |
| 2011/0177618 | A1 * | 7/2011 | Herr et al. ................ 436/515 |

FOREIGN PATENT DOCUMENTS

| | | |
|---|---|---|
| JP | 2007-518977 A | 7/2007 |
| JP | 2008-537119 A | 9/2008 |
| WO | WO 00/73799 A1 | 12/2000 |
| WO | WO 02/086332 A1 | 10/2002 |
| WO | WO 2006/102516 A2 | 9/2006 |
| WO | 2010135364 | 11/2010 |
| WO | 2011142781 | 11/2011 |

OTHER PUBLICATIONS

Fonslow et al. 'Free-Flow Electrophoresis on an Anodically Bonded Glass Microchip' Anal. Chem., Sep. 1, 2005, vol. 77(17), pp. 5706-5710.

He et al., 'Automated microfluidic protein immunoblotting' Nature Protocols, 2010, vol. 5(11), pp. 1844-1856.

He et al., 'Polyacrylamide Gel Photopatterning Enables Automated Protein Immunoblotting in a Two-Dimensional Microdevice' J. Am. Chem. Soc., 2010, vol. 132, pp. 2512-2513.

He et al., 'Microfluidic Polyacrylamide Gel Electrophoresis with in Situ Immunoblotting for Native Protein Analysis' Anal Chem, 2009, vol. 81, pp. 8177-8184.

Lerch et al., 'Electrokinetic Fluid Control in Two-Dimensional Planar Microfluidic Devices' Anal. Chem., Aug. 25, 2007, vol. 79(19), pp. 7485-7491.

Renzi, et al. 'Hand-held microanalytical instrument for chip-based electrophoretic separations of proteins' Anal Chem., Jan. 15, 2005, vol. 77(2), pp. 435-441.

Song, et al. 'Electrophoretic concentration of proteins at laser-patterned nanoporous membranes in microchips.' Anal Chem., Aug. 1, 2004, vol. 76(15), pp. 4589-4592.

Zeng et al., 'Microfluidic Self-patterning of Large-Scale Crystalline Nanoarrays for High-Throughput Continuous DNA Fractionation' Angew. Chem. Int. Ed., Jul. 15, 2008, vol. 47, pp. 6388-6391.

Zhang et al., "High-Speed Free-Flow Electrophoresis on Chip", Anal. Chem., vol. 75, pp. 5759-5766 (2003).

Office Action dated Jul. 8, 2014 issued in corresponding Japanese Patent Application No. 2012-511973.

* cited by examiner

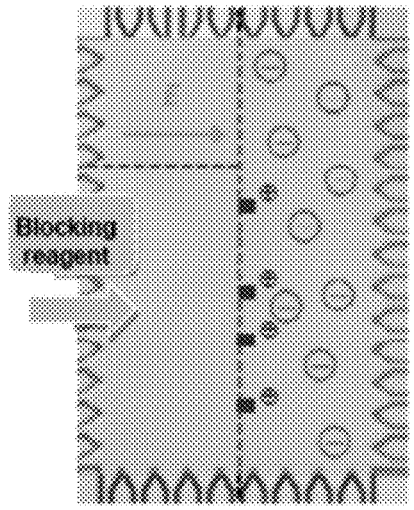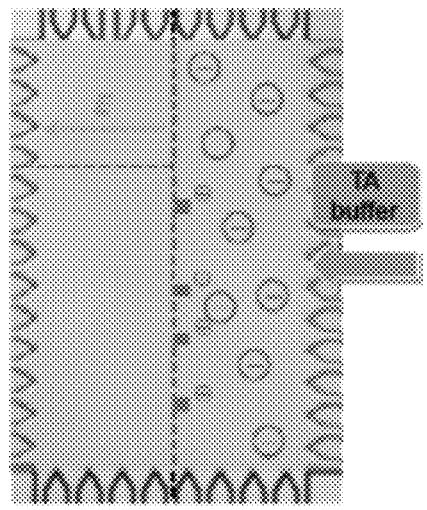
FIG. 3E        FIG. 3F
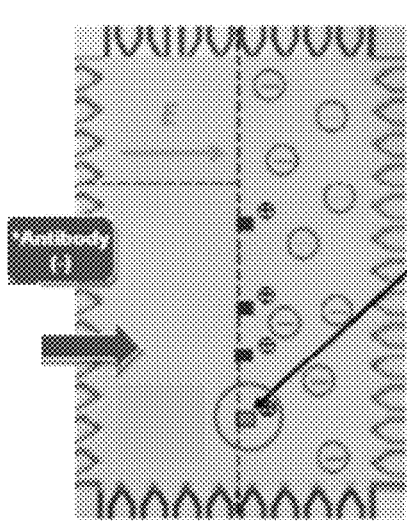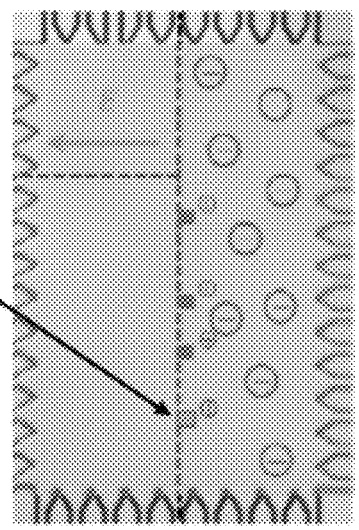
FIG. 3G        FIG. 3H

MULTI-DIRECTIONAL MICROFLUIDIC DEVICES COMPRISING A PAN-CAPTURE BINDING REGION

CROSS-REFERENCE TO RELATED APPLICATIONS

Pursuant to 35 U.S.C. §119(e), this application claims priority to U.S. Provisional Patent Application No. 61/416,693 filed on Nov. 23, 2010, the disclosure of which is herein incorporated by reference in its entirety.

INTRODUCTION

A variety of analytical techniques may be used to detect specific analytes in a given sample. For example, Western blotting can be used to detect proteins in a sample by using gel electrophoresis to separate the proteins in the sample followed by probing with antibodies specific for the target protein. Southern blotting combines transfer of electrophoresis-separated DNA fragments to a filter membrane and subsequent fragment detection by probe hybridization. Northern blotting involves the use of electrophoresis to separate RNA samples by size and detection with a hybridization probe complementary to part of or the entire target sequence. Eastern blotting can be used to detect protein post translational modifications (PTM) by analyzing electrophoresis-separated proteins for post-translational modifications using probes specific for lipids, carbohydrate, phosphorylation or any other protein modifications. Far-Western blotting is similar to Western blotting, but uses a non-antibody protein to bind the protein of interest, and thus can be used to detect protein-protein interactions. Southwestern blotting is a technique that can be used to detect DNA-binding proteins by using gel electrophoresis to separate the proteins in a sample followed by probing with genomic DNA fragments.

Conventional blotting techniques, as discussed above, may fall short of performance needs for applications that demand either high-throughput sample analysis or operation in resource poor settings. Blotting techniques may require labor-intensive, time consuming, multi-step procedures carried out by a trained technician, and thus may be impractical for use in a clinical setting. Furthermore, devices that are less expensive and easier to fabricate and operate are desired.

SUMMARY

Microfluidic devices and methods for using the same are provided. Aspects of the invention include microfluidic devices that include a separation medium and a pan-capture binding medium. The microfluidic devices are configured to subject a sample to two or more directionally distinct flow fields. Also provided are methods of using the devices as well as systems and kits that include the devices. The devices, systems and methods find use in a variety of different applications, including diagnostic and validation assays.

Aspects of the present disclosure include a microfluidic device for detecting an analyte in a fluid sample. In certain embodiments, the microfluidic device includes a separation medium having a separation flow path with a first directional axis, and a pan-capture binding medium in fluid communication with the separation medium and having a flow path with a second directional axis. In some cases, the second directional axis is orthogonal to the first directional axis.

The binding medium may be configured to non-specifically bind to analytes in the sample through electrostatic interactions. For instance, the binding medium may be configured to have a negative charge. In some instances, the binding medium includes a negatively charged gel. In certain embodiments, the binding medium includes a negatively charged pan-capture binding member stably associated with a support. In some cases, the fluid sample includes a detergent. The detergent may be configured to provide analytes in the sample with a positive charge. Embodiments that include a negatively charged gel and a detergent that gives analytes in the sample a positive charge may facilitate electrostatic binding of the analytes to the binding medium. In certain instances, the detergent is cetyltrimethylammonium bromide.

In some instances, the analyte includes a fluorescent label. In some instances, the microfluidic device is configured to subject a sample to two or more directionally distinct flow fields. For example, the two or more directionally distinct flow fields may include two or more directionally distinct electric fields. In certain cases, the microfluidic device includes a chamber containing the separation medium and the binding medium.

Aspects of the present disclosure also include a method of detecting an analyte in a fluid sample. The method includes: (a) introducing the fluid sample that includes the analyte into a microfluidic device configured to subject a sample to two or more directionally distinct flow fields; (b) directing the sample through the separation medium to produce a separated sample; and (c) detecting the analyte in the separated sample. As indicated above, the microfluidic device includes a separation medium having a separation flow path with a first directional axis, and a pan-capture binding medium in fluid communication with the separation medium and having a flow path with a second directional axis.

In certain embodiments, the method of detecting an analyte also includes transferring the separated sample to the binding medium. The method may also include contacting the analyte with a label that specifically binds to the analyte to produce a labeled analyte. In some cases, the method further includes detecting the labeled analyte.

In certain instances, the method is a diagnostic method, or in other instances may be a validation method.

Aspects of the present disclosure also include a system for detecting an analyte in a fluid sample. The system includes a microfluidic device configured to subject a sample to two or more directionally distinct flow fields, and a detector. As described above, the microfluidic device includes a separation medium having a separation flow path with a first directional axis, and a pan-capture binding medium in fluid communication with the separation medium and having a flow path with a second directional axis.

In certain embodiments, the system also includes microfluidic components configured to direct a fluid through the microfluidic device.

Aspects of the present disclosure also include a kit that includes a microfluidic device configured to subject a sample to two or more directionally distinct flow fields, and a buffer. As described above, the microfluidic device includes a separation medium having a separation flow path with a first directional axis, and a pan-capture binding medium in fluid communication with the separation medium and having a flow path with a second directional axis.

In certain embodiments, the buffer includes a detergent configured to provide analytes in the sample with a positive charge. For example, the detergent may be cetyltrimethylammonium bromide.

In certain embodiments, the kit also includes one or more reagents, such as, but not limited to, a detection reagent, a release reagent, a detergent, a refolding reagent and a denaturing reagent.

BRIEF DESCRIPTION OF THE FIGURES

FIGS. 3A-3H show schematics of the separation, transfer and detection of analytes in a sample, according to embodiments of the present disclosure.

FIG. 7 (bottom) shows a graph of a linear log-molecular mass (Mr) vs. mobility ($10^{-5}$ cm$^2$/V·s) relation for the separation of a protein sample in a microfluidic device, according to embodiments of the present disclosure.

DETAILED DESCRIPTION

Figure 1A:
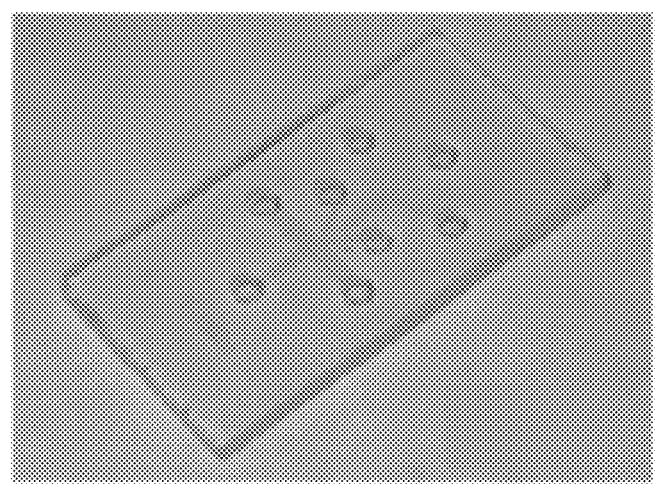
FIGS. 1A and 1B show a photograph and a schematic drawing of a microfluidic device, according to embodiments of the present disclosure.

Microfluidic devices and methods for using the same are provided. Aspects of the invention include microfluidic devices that include a separation medium and a pan-capture binding medium. The microfluidic devices are configured to subject a sample to two or more directionally distinct electric fields. Also provided are methods of using the devices as well as systems and kits that include the devices. The devices, systems and methods find use in a variety of different applications, including diagnostic and validation assays.

Below, the subject microfluidic devices are described first in greater detail. Methods of detecting an analyte in a fluid sample are also disclosed in which the subject microfluidic devices find use. In addition, systems and kits that include the subject microfluidic devices are also described.

Microfluidic Devices

Aspects of the present disclosure include microfluidic devices for detecting an analyte in a fluid sample. A "microfluidic device" is device that is configured to control and manipulate fluids geometrically constrained to a small scale (e.g., sub-millimeter). Embodiments of the microfluidic devices include a separation medium and a pan-capture binding medium. The separation medium may be configured to separate analytes in a sample from each other. The separated analytes may be contacted with the pan-capture binding medium, which non-specifically binds to components in the sample. The bound analyte or analytes of interest may then be detected. Additional details about the separation medium and pan-capture binding medium are discussed below.

Separation Medium

In certain embodiments, the microfluidic devices include a separation medium. The separation medium may be configured to separate analytes in a sample from each other. In some cases, the separation medium is configured to separate analytes in a sample based on the physical properties of the analytes. For example, the separation medium may be configured to separate the analytes in the sample based on the molecular mass, size, charge (e.g., charge to mass ratio), isoelectric point, etc. of the analytes. In certain instances, the separation medium is configured to separate the analytes in the sample based on the molecular mass of the analytes. In some cases, the separation medium is configured to separate the analytes in the sample based on the isoelectric point of the analytes (e.g., isoelectric point focusing). The separation medium may be configured to separate the analytes in the sample into distinct detectable bands of analytes. By "band" is meant a distinct detectable region where the concentration of an analyte is significantly higher than the surrounding regions. Each band of analyte may include a single analyte or several analytes, where each analyte in a single band of analytes has substantially similar physical properties, as described above.

In certain embodiments, the separation medium is configured to separate the analytes in a sample as the sample traverses the separation medium. In some cases, the separation medium is configured to separate the analytes in the sample as the sample flows through the separation medium. Aspects of the separation medium include that the separation medium has a flow path with a directional axis. By "flow path" is meant the direction a fluid sample travels as it moves. In some instances, the flow path is the direction the sample travels as the sample traverses a medium, such as the separation medium. As indicated above, the separation medium may have a flow path with a directional axis. In some embodiments, the directional axis of the separation flow path is aligned with the length of the separation medium. In these embodiments, the sample traverses the separation medium in the direction of the separation flow path of the separation medium (e.g., the sample may traverse the separation medium along the length of the separation medium). In some cases, the length of the separation medium is greater than the width of the separation medium, such as 2 times, 3 times, 4 times, 5 times, 10 times, etc. the width of the separation medium. In some instances, the separation flow path of the separation medium is defined by a region that includes the separation medium. For example, the microfluidic device may include a chamber. The chamber may include a separation region that includes the separation medium and a binding region that includes the pan-capture binding medium. The separation medium may be included in the chamber, such that a sample traverses the separation medium as the sample flows through the chamber.

In certain embodiments, the separation medium includes a polymer, such as a polymeric gel. The polymeric gel may be a gel suitable for gel electrophoresis. The polymeric gel may include, but is not limited to, a polyacrylamide gel, an agarose gel, and the like. The resolution of the separation medium may depend on various factors, such as, but not limited to, pore size, total polymer content (e.g., total acrylamide content), concentration of cross-linker, applied electric field, assay time, and the like. For instance, the resolution of the separation medium may depend on the pore size of the separation medium. In some cases, the pore size depends on the total polymer content of the separation medium and/or the concentration of cross-linker in the separation medium. In certain instances, the separation medium is configured to resolve analytes with molecular mass differences of 50,000 Da or less, or 25,000 Da or less, or 10,000 Da or less, such as 7,000 Da or less, including 5,000 Da or less, or 2,000 Da or less, or 1,000 Da or less, for example 500 Da or less, or 100 Da or less. In some cases, the separation medium may include a polyacrylamide gel that has a total acrylamide content, T (T=total concentration of acrylamide and bisacrylamide monomer), ranging from 1% to 20%, such as from 3% to 15%, including from 5% to 10%. In some instances, the separation medium has a total acrylamide content of 6%.

In certain embodiments, the separation medium includes a buffer. The buffer may be any convenient buffer used for gel electrophoresis. In certain embodiments, the buffer is an alkaline buffer, such as, but not limited to, a tricine-arginine buffer. In certain embodiments, the separation medium includes a buffer, such as a Tris-glycine buffer. For example, the buffer may include a mixture of Tris and glycine.

In some cases, the buffer includes a detergent. In certain instances, the detergent is configured to provide analytes in the sample with substantially similar charge-to-mass ratios. Analytes with substantially similar charge-to-mass ratios may facilitate the separation of the analytes into one or more bands in the separation medium based on the molecular masses of the analytes in the sample. In certain cases, the detergent is a cationic detergent configured to provide analytes in the sample with a charge, such as a positive charge. For example, the detergent may be a cationic detergent configured to provide analytes in the sample with a positive charge. Analytes with a positive charge may facilitate electrostatic binding of the analytes to a negatively charged binding medium, as discussed in further detail below. In some embodiments, the detergent is cetyltrimethylammonium bromide (CTAB), also known as cetrimonium bromide or hexadecyltrimethylammonium bromide.

In some instances, as described above, the buffer includes a detergent. Certain embodiments of the buffer may include an anionic detergent. In certain cases, the detergent is an anionic detergent configured to provide analytes in the sample with a negative charge. Analytes with a negative charge may facilitate electrostatic binding of the analytes to a positively charged binding medium. For instance, the detergent may be an anionic detergent, such as, but not limited to, sodium dodecyl sulfate (SDS).

Pan-Capture Binding Medium

Aspects of the microfluidic devices include a pan-capture binding medium. By "pan-capture" is meant that the binding medium non-specifically binds to analytes in a sample. For example, a pan-capture binding medium may non-specifically bind to proteins in a sample. Non-specific binding may include binding to substantially all of the analytes in a sample. In some cases, non-specific binding is based on a binding interaction between the analytes in a sample and the pan-capture binding medium. The binding interaction can be based on one or more of a variety of binding interactions between the pan-capture binding medium and the analytes in the sample, such as, but not limited to, covalent bonds, ionic bonds, electrostatic interactions, hydrophobic interactions, hydrogen bonds, van der Waals forces (e.g., London dispersion forces), dipole-dipole interactions, combinations thereof, and the like. The binding interactions may be substantially permanent (e.g., requiring a relatively large amount of energy to overcome the binding interaction, such as with covalent bonds) or may be reversible (e.g., requiring a relatively low amount of energy to disrupt the binding interaction, such as with dipole-dipole interactions).

In certain embodiments, the pan-capture binding medium is configured to non-specifically bind to analytes in the sample through electrostatic interactions. In some cases, electrostatic interactions include binding interactions due to the attraction between two oppositely charged ions. For example, electrostatic interactions may be present between a positively charged analyte and a negatively charged binding medium. Similarly, electrostatic interactions may be present between a negatively charged analyte and a positively charged binding medium. In certain instances, the binding medium is configured to have a negative charge. As such, the negatively charged binding medium may be configured to have electrostatic binding interactions with positively charged analytes. In other instances, the binding medium is configured to have a positive charge. As such, the negatively charged binding medium may be configured to have electrostatic binding interactions with positively charged analytes.

In certain cases, the binding medium includes a polymer, such as a polymeric gel or polymeric monolith. By monolith is meant a single, contiguous structure. Monoliths may include a single region with the same physical and chemical composition, or may include two or more regions that differ in terms of their physical and chemical compositions. The polymeric gel may be a gel suitable for gel electrophoresis. The polymeric gel may include, but is not limited to, a polyacrylamide gel, an agarose gel, and the like. The polymeric gel may include polymers, such as, but is not limited to, acrylate polymers, alkylacrylate polymers, alkyl alkylacrylate polymers, copolymers thereof, and the like. In some cases, the binding medium may include a polyacrylamide gel that has a total acrylamide content ranging from 1% to 20%, such as from 3% to 15%, including from 5% to 10%. For instance, the binding medium may include a polyacrylamide gel with a total acrylamide content of 9%.

As described above, in certain embodiments, the binding medium is configured to have a negative charge. For instance, the binding medium may include a negatively charged gel, such as a negatively charged polyacrylamide gel. A negatively charged gel may facilitate electrostatic binding interactions with positively charged analytes. In certain embodiments, the binding medium includes a buffer. In some cases, the buffer is an alkaline buffer. Alkaline buffers may facilitate the presence of a negative charge on the binding medium (e.g., the polyacrylamide gel). In some instances, the buffer is an alkaline buffer, such as, but not limited to, a tricine-arginine buffer.

In other embodiments, the binding medium is configured to have a positive charge. For instance, the binding medium may include a positively charged gel, such as a positively charged polyacrylamide gel. A positively charged gel may facilitate electrostatic binding interactions with negatively charged analytes. As described above, the binding medium may include a buffer. In some cases, the buffer may be configured facilitate the presence of a positive charge on the binding medium, which in turn may facilitate electrostatic binding interactions with negatively charged analytes.

In certain embodiments, the binding medium includes a pan-capture binding member. The pan-capture binding member may be configured to bind to and retain analytes in a sample. For example, the pan-capture binding member may be configured to non-specifically bind to analytes in the sample, such as non-specifically binding to proteins in the sample. Similar to the pan-capture binding medium described above, the pan-capture binding member may be configured to bind to analytes based on one or more of a variety of binding interactions between the pan-capture binding member and the analytes in the sample, such as, but not limited to, covalent bonds, ionic bonds, electrostatic interactions, hydrophobic interactions, hydrogen bonds, van der Waals forces (e.g., London dispersion forces), dipole-dipole interactions, combinations thereof, and the like. In certain embodiments, the pan-capture binding member is configured to non-specifically bind to analytes in the sample through electrostatic interactions. For instance, the pan-capture binding member may be configured to have a negative charge, such that the pan-capture binding member non-specifically binds to positively charged analytes in the sample. In some instances, the pan-capture binding member includes a negatively charged compound, such as, but not limited to, negatively charged acrylamido compounds (e.g., Immobilines). In some cases, the pan-capture binding member includes a peptide or protein (e.g., a capture protein), such as a negatively charged protein or peptide. For example, the pan-capture binding member may include immunoglobulin-G (IgG), β-galactosidase (β-gal), myosin, derivatives thereof, combinations thereof, and the like. As described above, buffers, such as alkaline buffers (e.g., a tricine-arginine buffer), may facilitate the presence of a negative charge on the binding member. In some instances, an alkaline buffer ionizes acidic amino acid residues to provide a negative charge on the binding member (e.g., the acidic amino acid residues may have a lower pK value than the pH of the alkaline buffer).

In other embodiments, the pan-capture binding member may be configured to non-specifically bind to analytes in the sample through electrostatic interactions, such that the pan-capture binding member is configured to have a positive charge. For example, the pan-capture binding member may be configured to have a positive charge, such that the pan-capture binding member non-specifically binds to negatively charged analytes in the sample.

In certain embodiments, the pan-capture binding member is stably associated with a support. By "stably associated" is meant that, under standard conditions, a moiety is bound to or otherwise associated with another moiety or structure. In certain instances, the support is a polymeric gel, as described above. As such, in certain embodiments, the microfluidic devices include both a pan-capture binding medium and a pan-capture binding member, as described herein. Bonds between the binding member and the support may include covalent bonds and non-covalent interactions, such as, but not limited to, ionic bonds, electrostatic interactions, hydrophobic interactions, hydrogen bonds, van der Waals forces (e.g., London dispersion forces), dipole-dipole interactions, and the like. In certain embodiments, the binding member may be covalently bound to the support, such as cross-linked or copolymerized to the support. For example, the binding member may be bound to the support through a linking group, such as, but not limited to: a receptor/ligand binding pair; a ligand-binding portion of a receptor; an antibody/antigen binding pair; an antigen-binding fragment of an antibody; a hapten; a lectin/carbohydrate binding pair; an enzyme/substrate binding pair; a biotin/avidin binding pair; a biotin/streptavidin binding pair; a digoxin/antidigoxin binding pair; a DNA or RNA aptamer binding pair; a peptide aptamer binding pair; and the like. In some cases, the binding member is bound to the support through a biotin/streptavidin binding pair.

Further Aspects of Embodiments of the Microfluidic Devices

Aspects of the microfluidic devices include embodiments where the separation medium is in fluid communication with the binding medium. The microfluidic device may be configured to direct a sample through the separation medium first to produce a separated sample. In certain embodiments, the microfluidic device is configured such that the separation medium and the binding medium are in direct fluid communication with each other. For example, the separation medium may be in direct contact with the binding medium. In some cases, the separation medium and the binding medium are bound to each other, such as contiguously photopatterned side-by-side. Embodiments where the separation medium is in direct fluid communication with the binding medium may facilitate the transfer of components from the separation medium to the binding medium with a minimal loss of components. In some instances, the microfluidic devices are configured such that components are quantitatively and reproducibly transferred from the separation medium to the binding medium.

In certain embodiments, the microfluidic device is configured to direct the separated sample to the binding medium. In other cases, the microfluidic device is configured such that the separation medium and the binding medium are in direct fluid communication with each other, such that a sample or analyte can traverse directly from the separation medium to the binding medium. As described above, the binding medium may be configured to non-specifically bind to analytes in the sample for detection of an analyte of interest in the separated sample.

In certain embodiments, the microfluidic devices are multi-directional microfluidic devices. By "multi-directional" is meant more than one direction, such as two or more directions, three or more directions, four or more directions, etc. In certain cases, two or more directions are included in a single plane, such that the two or more directions are co-planar. In some instances, the microfluidic devices are configured to direct a fluid in more than one direction (e.g., the microfluidic devices are multi-directional), such as two or more directions, three or more directions, four or more directions, etc. For example, the microfluidic devices may be configured to direct a fluid in two directions, three directions, four directions, etc. For instance, the microfluidic devices may be included in a substrate, such that the microfluidic device is planar. The microfluidic device may be configured to direct fluids in multiple directions within that plane.

Aspects of the microfluidic devices include a separation medium having a separation flow path and a pan-capture binding medium in fluid communication with the separation medium. The separation medium may include a separation flow path with a first directional axis, which corresponds to the direction the sample travels as the sample traverses the separation medium. The binding medium may have a second flow path with a second directional axis. In some instances, the second flow path is the direction the sample travels as the sample traverses from the separation medium to the binding medium. The binding medium may have a directional axis different from the directional axis of the separation medium. For example, the separation medium may have a first directional axis and the binding medium may have a second directional axis, where the second directional axis is at an angle of 180 degrees or less with respect to the first directional axis, such as 150 degrees or less, 135 degrees or less, including 120 degrees or less, 90 degrees or less, 60 degrees or less, 45 degrees or less, or 30 degrees or less with respect to the first directional axis. In certain embodiments, the second directional axis is orthogonal to the first directional axis, such that the separation flow path is at a 90 degree angle with respect to the flow path of the binding medium.

In some instances, the microfluidic device is configured to subject a sample to two or more directionally distinct flow fields. By "flow field" is meant a region where components traverse the region in substantially the same direction. For example, a flow field may include a region where mobile components move through a medium in substantially the same direction. A flow field may include a medium, such as a separation medium, a binding medium, a loading medium, etc., where components, such as buffers, analytes, reagents, etc., move through the medium in substantially the same direction. A flow field may be induced by an applied electric field, a pressure differential, electroosmosis, and the like. In some embodiments, the two or more flow fields may be directionally distinct. For example, a first flow field may be aligned with the directional axis of the separation flow path of the separation medium. The first flow field may be configured to direct the sample or analytes through the separation medium along the separation flow path. A second flow field may be aligned with the directional axis of the flow path of the binding medium. In some instances, the second flow field is configured to direct the sample or analytes from the separation medium to the binding medium along the flow path of the binding medium. The second flow field may be configured to direct the sample or analytes from the separation medium to the binding medium such that the analytes contact and bind to the binding medium. As described above, in certain instances, the directional axis of the binding medium flow path is orthogonal to the directional axis of the separation flow path. In these instances, the second flow field may be orthogonal to the first flow field.

In certain embodiments, the microfluidic device is configured to subject a sample to two or more directionally distinct electric fields. The electric fields may facilitate the movement of the sample through the microfluidic device (e.g., electrokinetic transfer of the sample from one region of the microfluidic device to another region of the microfluidic device). The electric fields may also facilitate the separation of the analytes in the sample by electrophoresis (e.g., polyacrylamide gel electrophoresis (PAGE)), as described above. For instance, the electric field may be configured to direct the analytes in a sample through the separation medium of the microfluidic device. The electric field may be configured to facilitate the separation of the analytes in a sample based on the physical properties of the analytes. For example, the electric field may be configured to facilitate the separation of the analytes in the sample based on the molecular mass, size, charge (e.g., charge to mass ratio), isoelectric point, etc. of the analytes. In certain instances, the electric field is configured to facilitate the separation of the analytes in the sample based on the molecular mass of the analytes.

In some embodiments, the two or more electric fields may be directionally distinct. For example, a first electric field may be aligned with the directional axis of the separation flow path of the separation medium. The first electric field may be configured to direct the sample or analytes through the separation medium along the separation flow path. A second electric field may be aligned with the directional axis of the flow path of the binding medium. In some instances, the second electric field is configured to direct the sample or analytes from the separation medium to the binding medium along the flow path of the binding medium. The second electric field may be configured to direct the analytes from the separation medium to the binding medium such that the analytes contact and bind to the binding medium. As described above, in certain instances, the directional axis of the binding medium flow path is orthogonal to the directional axis of the separation flow path. In these instances, the second electric field may be orthogonal to the first electric field.

In certain embodiments, the microfluidic device includes one or more electric field generators configured to generate an electric field. The electric field generator may be configured to apply an electric field to various regions of the microfluidic device, such as one or more of the separation medium, the binding medium, the loading medium, and the like. The electric field generators may be configured to electrokinetically transport the analytes and components in a sample through the various media in the microfluidic device. In certain instances, the electric field generators may be proximal to the microfluidic device, such as arranged on the microfluidic device. In some cases, the electric field generators are positioned a distance from the microfluidic device. For example, the electric field generators may be incorporated into a system for detecting an analyte, as described in more detail below.

Embodiments of the microfluidic device may be made of any suitable material that is compatible with the assay conditions, samples, buffers, reagents, etc. used in the microfluidic device. In some cases, the microfluidic device is made of a material that is inert (e.g., does not degrade or react) with respect to the samples, buffers, reagents, etc. used in the subject microfluidic device and methods. For instance, the microfluidic device may be made of materials, such as, but not limited to, glass, quartz, polymers, elastomers, paper, combinations thereof, and the like.

In some instances, the microfluidic device includes one or more sample input ports. The sample input port may be configured to allow a sample to be introduced into the microfluidic device. The sample input port may be in fluid communication with the separation medium. In some instances, the sample input port is in fluid communication with the upstream end of the separation medium. The sample input port may further include a structure configured to prevent fluid from exiting the sample input port. For example, the sample input port may include a cap, valve, seal, etc. that may be, for instance, punctured or opened to allow the introduction of a sample into the microfluidic device, and then re-sealed or closed to substantially prevent fluid, including the sample and/or buffer, from exiting the sample input port.

In certain embodiments, the microfluidic device is substantially transparent. By "transparent" is meant that a substance allows visible light to pass through the substance. In some embodiments, a transparent microfluidic device facilitates detection of analytes bound to the binding medium, for example analytes that include a detectable label, such as a fluorescent label. In some cases, the microfluidic device is substantially opaque. By "opaque" is meant that a substance does not allow visible light to pass through the substance. In certain instances, an opaque microfluidic device may facilitate the analysis of analytes that are sensitive to light, such as analytes that react or degrade in the presence of light.

Figure 2:
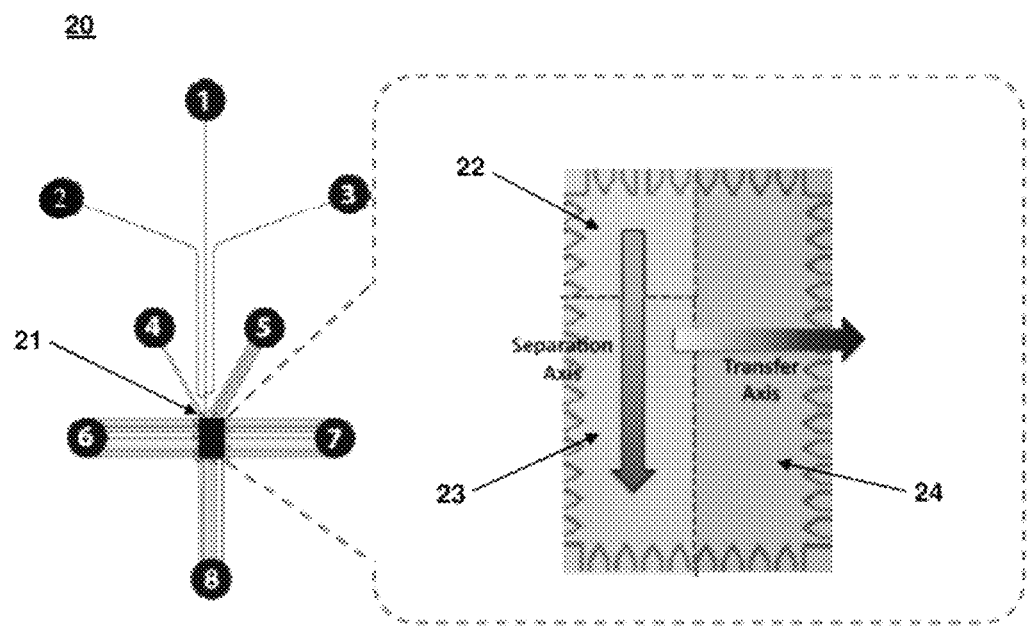
FIG. 2 shows a schematic drawing of a microfluidic device and an enlargement of the chamber that includes a loading medium, a separation medium and a binding medium, according to embodiments of the present disclosure.

In some aspects, the separation medium and the binding medium are provided in a single common chamber, as illustrated in FIG. 2. In these embodiments, the microfluidic device includes a chamber. The chamber may include a separation medium and a binding medium. As described above, the separation medium may be in fluid communication, such as in direct physical contact, with the binding medium. In some cases, the separation medium is bound to the binding medium, such as contiguously photopatterned side-by-side with the binding medium. As such, the chamber may be configured to contain both the separation medium and the binding medium in fluid communication with each other.

In addition to the separation medium and the binding medium, the chamber may also include a loading medium. The loading medium may be in fluid communication with the separation medium. In some instances, the loading medium is in direct physical contact with the separation medium. For example, the loading medium may be bound to the separation medium, such as contiguously photopatterned side-by-side with the separation medium. The loading medium may be positioned such that the sample contacts the loading medium before contacting the separation medium. In certain embodiments, the loading medium facilitates contacting a sample with the separation medium. For instance, the loading medium may be configured to concentrate the sample before the sample contacts the separation medium. In certain embodiments, the loading medium may include two or more regions that have different physical and/or chemical properties. The loading medium may include a loading region and a stacking region. The loading medium may be configured to include a loading region upstream from a stacking region.

In certain embodiments, the loading medium includes a polymer, such as a polymeric gel. The polymeric gel may be a gel suitable for gel electrophoresis. The polymeric gel may include, but is not limited to, a polyacrylamide gel, an agarose gel, and the like. In some cases, the loading region includes a polymeric gel with a large pore size. For example, the loading region may include a polyacrylamide gel that has a total acrylamide content of 5% or less, such as 4% or less, including 3% or less, or 2% or less. In some instances, the loading region has a total acrylamide content of 3%. In some cases, the stacking region of the loading medium may be configured to concentrate the sample before the sample contacts the separation medium. The stacking region may include a polymeric gel with a smaller pore size than the loading region. For example, the stacking region may include a polyacrylamide gel that has a total acrylamide content of ranging from 5% to 10%, such as from 5% to 9%, including from 5% to 8%, or from 5% to 7%. In some instances, the stacking region has a total acrylamide content of 6%. The smaller pore size of the stacking region may slow the electrophoretic movement of the sample through the stacking region, thus concentrating the sample before it contacts the separation medium.

In certain instances, the chamber contains the loading medium, the separation medium and the binding medium. The chamber may be configured to contain the loading medium, the separation medium and the binding medium such that the loading medium, the separation medium and the binding medium are in fluid communication with each other, as described above. For example, the chamber may include a contiguous polymeric gel monolith with various regions. Each region of the contiguous polymeric gel monolith may have different physical and/or chemical properties. The contiguous polymeric gel monolith may include a first region having a loading medium, a second region having a separation medium and a third region having a binding medium. The flow paths of each region of the polymeric gel monolith may be configured such that a sample first contacts the loading medium, then contacts the separation medium, and finally contacts the binding medium.

In certain embodiments, the polymeric gel monolith has a width ranging from 0.1 mm to 5 mm, such as from 0.2 mm to 2.5 mm, including from 0.5 mm to 1.5 mm. In some cases, the polymeric gel monolith has a width of 1 mm. In some instances, the polymeric gel monolith has a length ranging from 0.5 mm to 5 mm, such as from 0.5 mm to 3 mm, including from 1 mm to 2 mm. In certain instances, the polymeric gel monolith has a length of 1.5 mm. In certain embodiments, the first region of the polymeric gel monolith that includes the loading medium has a width ranging from 0.1 mm to 5 mm, such as from 0.2 mm to 2.5 mm, including from 0.5 mm to 1.5 mm. In some cases, the first region of the polymeric gel monolith that includes the loading medium has a width of 0.9 mm. In some cases, the first region of the polymeric gel monolith that includes the loading medium has a length ranging from 0.1 mm to 2 mm, such as from 0.1 mm to 1 mm, including from 0.1 mm to 0.5 mm. In certain embodiments, the first region of the polymeric gel monolith that includes the loading medium has a length of 0.2 mm. In certain instances, the second region of the polymeric gel monolith that includes the separation medium has a width ranging from 0.1 mm to 5 mm, such as from 0.2 mm to 2.5 mm, including from 0.5 mm to 1.5 mm. In some cases, the second region of the polymeric gel monolith that includes the separation medium has a width of 0.9 mm. In some cases, the second region of the polymeric gel monolith that includes the separation medium has a length ranging from 0.5 mm to 5 mm, such as from 0.5 mm to 3 mm, including from 1 mm to 2 mm. In certain embodiments, the second region of the polymeric gel monolith that includes the separation medium has a length of 1.3 mm. In certain instances, the third region of the polymeric gel monolith that includes the binding medium has a width ranging from 0.01 mm to 2 mm, such as from 0.01 mm to 1 mm, including from 0.05 mm to 0.5 mm.

In some cases, the third region of the polymeric gel monolith that includes the bonding medium has a width of 0.1 mm. In some cases, the third region of the polymeric gel monolith that includes the binding medium has a length ranging from 0.5 mm to 5 mm, such as from 0.5 mm to 3 mm, including from 1 mm to 2 mm. In certain embodiments, the third region of the polymeric gel monolith that includes the binding medium has a length of 1.5 mm.

In certain embodiments, the microfluidic device has a width ranging from 10 cm to 1 mm, such as from 5 cm to 5 mm, including from 1 cm to 5 mm. In some instances, the microfluidic device has a length ranging from 100 cm to 1 mm, such as from 50 cm to 1 mm, including from 10 cm to 5 mm, or from 1 cm to 5 mm. In certain aspects, the microfluidic device has an area of 1000 $cm^2$ or less, such as 100 $cm^2$ or less, including 50 $cm^2$ or less, for example, 10 $cm^2$ or less, or 5 $cm^2$ or less, or 3 $cm^2$ or less, or 1 $cm^2$ or less, or 0.5 $cm^2$ or less, or 0.25 $cm^2$ or less, or 0.1 $cm^2$ or less.

Further aspects of related microfluidic devices are found in U.S. application Ser. No. 13/055,679, filed Jan. 24, 2011, the disclosure of which is incorporated herein by reference in its entirety.

Figure 1B:
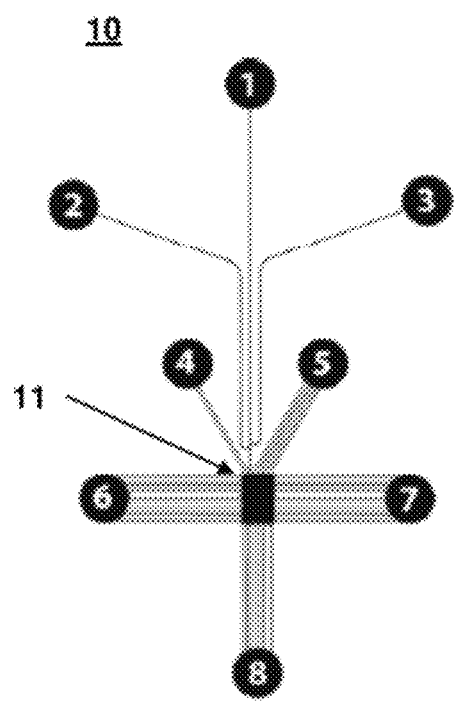

FIG. 1A shows a photograph of a microfluidic device 10. As shown in FIG. 1B, the microfluidic device 10 includes a chamber 11 that contains the loading medium, the separation medium and the binding medium. The microfluidic device 10 also includes various microfluidic channels, such as inlet channels 1, 2, and 3, and control channels 4, 5, 6, 7, and 8. Each microfluidic channel has a corresponding access port (represented by the black dots).

FIG. 2 shows a schematic of a microfluidic device 20 that includes a chamber 21 that contains a loading medium 22, a separation medium 23 and a binding medium 24. The loading medium 22 is in fluid communication with the separation medium 23, which is in fluid communication with the binding medium 24. The directional axis of the separation medium 23 is shown by the vertical arrow and indicates the flow path a sample traverses from the loading medium 22 to the separation medium 23 and also through the separation medium 23. The directional axis of the binding medium 24 is shown by the horizontal arrow and indicates the flow path a sample traverses from the separation medium 23 to the binding medium 24. The microfluidic device 20 also includes various microfluidic channels, such as inlet channels 1, 2, and 3, and control channels 4, 5, 6, 7, and 8. Inlet channels 1, 2, and 3 may be configured to direct a fluid sample into the chamber 21. Control channels 4, 5, 6, 7, and 8 may be configured to direct fluids (e.g., reagents, labels, buffers, wash fluids, etc.) into and/or away from the chamber 21. In addition, control channels 4, 5, 6, 7, and 8 may be configured to apply an electric field to various regions of the microfluidic device for electrokinetically transporting analytes in a sample through the loading medium 22, the separation medium 23 and the binding medium 24 in the chamber 21.

Methods

Embodiments of the methods are directed to determining whether an analyte is present in a sample, e.g., determining the presence or absence of one or more analytes in a sample. In certain embodiments of the methods, the presence of one or more analytes in the sample may be determined qualitatively or quantitatively. Qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which an exact measurement of the concentration of the analyte is provided to the user.

In certain embodiments, the microfluidic devices are configured to detect the presence of one or more analytes in a sample. The method includes introducing a fluid sample into a microfluidic device. Introducing the fluid sample into the microfluidic device may include contacting the sample with the separation medium, or in embodiments of the microfluidic devices that include a loading medium, contacting the sample with the loading medium. The method further includes directing the sample through the separation medium to produce a separated sample. In some cases, the separated sample is produced by gel electrophoresis as the sample traverses the separation medium, as described above. The separated sample may include distinct detectable bands of analytes, where each band includes one or more analytes that have substantially similar properties, such as molecular mass, size, charge (e.g., charge to mass ratio), isoelectric point, etc. depending on the type of gel electrophoresis performed.

Aspects of the methods may also include transferring the separated sample to a pan-capture binding medium. In some embodiments, the method includes transferring the entire separated sample to the pan-capture binding medium. In other cases, specific bands of analytes in the separated sample may be selectively transferred to the binding medium. In some cases, the method includes contacting the analytes in the separated sample with the pan-capture binding medium. As described above, the pan-capture binding medium may be configured to non-specifically bind to analytes, thus retaining substantially all the analytes in the binding medium.

In certain embodiments, the method includes detecting an analyte of interest bound to the binding medium. Detectable binding of an analyte of interest to the binding medium indicates the presence of the analyte of interest in the sample. In some instances, detecting the analyte of interest includes contacting the analyte of interest with a label configured to specifically bind to the analyte of interest. The label can be any molecule that specifically binds to a protein or nucleic acid sequence or biomacromolecule that is being targeted (e.g., the analyte of interest). Depending on the nature of the analyte, the label can be, but is not limited to: single strands of DNA complementary to a unique region of the target DNA or RNA sequence for the detection of nucleic acids; antibodies against an epitope of a peptidic analyte for the detection of proteins and peptides; or any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like. In certain embodiments, the label includes an antibody. The antibody may specifically bind to the analyte of interest.

In certain embodiments, the label includes a detectable label. Detectable labels include any convenient label that may be detected using the methods and systems, and may include, but are not limited to, fluorescent labels, colorimetric labels, chemiluminescent labels, multicolor reagents, enzyme-linked reagents, avidin-streptavidin associated detection reagents, radiolabels, gold particles, magnetic labels, and the like. In embodiments, the label includes an antibody associated with a detectable label. For example, the label may include a fluorescently labeled antibody that specifically binds to the analyte of interest.

Samples that may be assayed with the subject methods may include both simple and complex samples. Simple samples are samples that include the analyte of interest, and may or may not include one or more molecular entities that are not of interest, where the number of these non-interest molecular entities may be low, e.g., 10 or less, 5 or less, etc. Simple samples may include initial biological or other samples that have been processed in some manner, e.g., to remove potentially interfering molecular entities from the sample. By "complex sample" is meant a sample that may or may not have the analyte of interest, but also includes many different proteins and other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities, that differ from each other in terms of molecular structure or physical properties (e.g., molecular mass, size, charge, isoelectric point, etc.).

In certain embodiments, the samples of interest are biological samples, such as, but not limited to, urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like. The sample can be a biological sample or can be extracted from a biological sample derived from humans, animals, plants, fungi, yeast, bacteria, tissue cultures, viral cultures, or combinations thereof using conventional methods for the successful extraction of DNA, RNA, proteins and peptides. In certain embodiments, the sample is a fluid sample, such as a solution of analytes in a fluid. The fluid may be an aqueous fluid, such as, but not limited to water, a buffer, and the like.

As described above, the samples that may be assayed in the subject methods may include one or more analytes of interest. Examples of detectable analytes include, but are not limited to: nucleic acids, e.g., double or single-stranded DNA, double or single-stranded RNA, DNA-RNA hybrids, DNA aptamers, RNA aptamers, etc.; proteins and peptides, with or without modifications, e.g., antibodies, diabodies, Fab fragments, DNA or RNA binding proteins, phosphorylated proteins (phosphoproteomics), peptide aptamers, epitopes, and the like; small molecules such as inhibitors, activators, ligands, etc.; oligo or polysaccharides; mixtures thereof; and the like.

In certain embodiments, the method includes concentrating, diluting, or buffer exchanging the sample prior to directing the sample through the separation medium. Concentrating the sample may include contacting the sample with a concentration medium prior to contacting the sample with the separation medium. The concentration medium may include a small pore size polymeric gel, a membrane (e.g., a size exclusion membrane), combinations thereof, and the like. Concentrating the sample prior to contacting the sample with the separation medium may facilitate an increase in the resolution between the bands of analytes in the separated sample because each separated band of analyte may disperse less as the sample traverses through the separation medium. Diluting the sample may include contacting the sample with additional buffer prior to contacting the sample with the separation medium. Buffer exchanging the sample may include contacting the sample with a buffer exchange medium prior to contacting the sample with the separation medium. The buffer exchange medium may include a buffer different from the sample buffer. The buffer exchange medium may include, but is not limited to, a molecular sieve, a porous resin, and the like.

In certain embodiments, the method includes contacting the separated analytes bound to the binding medium with a blocking reagent prior to detecting the analyte of interest. In some cases, contacting the separated analytes with a blocking reagent prior to detecting the analyte of interest may facilitate a minimization in non-specific binding of a detectable label to the separated analytes. For example, contacting the separated analytes with the blocking reagent prior to detecting the analyte of interest may facilitate a minimization in non-specific binding of a labeled antibody to the separated analytes. The blocking reagent can be any blocking reagent that functions as described above, and may include, but is not limited to, bovine serum albumin (BSA), non-fat dry milk, casein, and gelatin. In certain embodiments, the method also includes optional washing steps, which may be performed at various times before, during and after the other steps in the method. For example, a washing step may be performed after transferring the separated sample from the separation medium to the binding medium, after contacting the separated sample with the blocking reagent, after contacting the separated sample with the detectable label, etc.

Embodiments of the method may also include releasing the analyte bound to the binding medium. The releasing may include contacting the bound analyte with a releasing agent. The releasing agent may be configured to disrupt the binding interaction between the analyte and the binding medium. In some cases, the releasing agent is a reagent, buffer, or the like, that disrupts the binding interaction between the analyte and the binding medium causing the binding medium to release the analyte. After releasing the analyte from the binding medium, the method may include transferring the analyte away from the binding medium. For example, the method may include directing the released analyte downstream from the binding medium for secondary analysis with a secondary analysis device such as, but is not limited to, a UV spectrometer, and IR spectrometer, a mass spectrometer, an HPLC, an affinity assay device, and the like.

In some embodiments, the methods include the uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the methods include the uniplex analysis of the sample to determine the presence of the analyte of interest in the sample mixture.

Certain embodiments include the multiplex analysis of two or more analytes in a sample. By "multiplex analysis" is meant that the presence two or more distinct analytes, in which the two or more analytes are different from each other, is determined. For example, analytes may include detectable differences in their molecular mass, size, charge (e.g., mass to charge ratio), isoelectric point, and the like. In some instances, the number of analytes is greater than 2, such as 4 or more, 6 or more, 8 or more, etc., up to 20 or more, e.g., 50 or more, including 100 or more, distinct analytes. In certain embodiments, the methods include the multiplex analysis of 2 to 100 distinct analytes, such as 4 to 50 distinct analytes, including 4 to 20 distinct analytes. In certain embodiments, multiplex analysis also includes the use of two or more different detectable labels. The two or more different detectable labels may specifically bind to the same or different analytes. In some cases, the two or more different detectable labels may specifically bind to the same analyte. For instance, the two or more different detectable labels may include different antibodies specific for different epitopes on the same analyte. The use of two or more detectable labels specific for the same analyte may facilitate the detection of the analyte by improving the signal-to-noise ratio. In other cases, the two or more different detectable labels may specifically bind to different analytes. For example, the two or more detectable labels may include different antibodies specific for epitopes on different analytes. The use of two or more detectable labels each specific for different analytes may facilitate the detection of two or more respective analytes in the sample in a single assay.

In certain embodiments, the method is an automated method. As such, the method may include a minimum of user interaction with the microfluidic devices and systems after introducing the sample into the microfluidic device. For example, the steps of directing the sample through the separation medium to produce a separated sample and transferring the separated sample to the binding medium may be performed by the microfluidic device and system, such that the user need not manually perform these steps. In some cases, the automated method may facilitate a reduction in the total assay time. For example, embodiments of the method, including the separation and detection of analytes in a sample, may be performed in 30 min or less, such as 20 min or less, including 15 min or less, or 10 min or less, or 5 min or less, or 2 min or less, or 1 min or less.

Figure 3A:
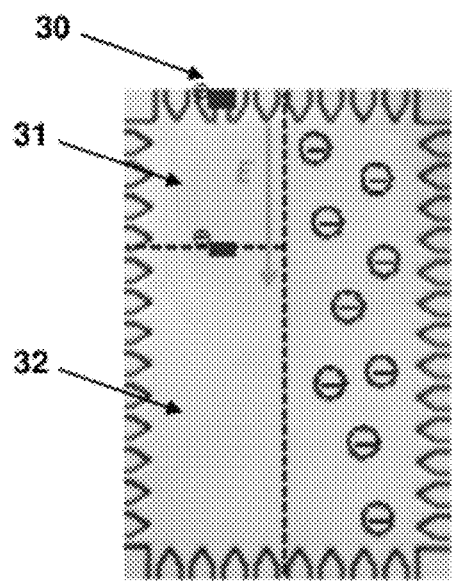
Figure 3B:
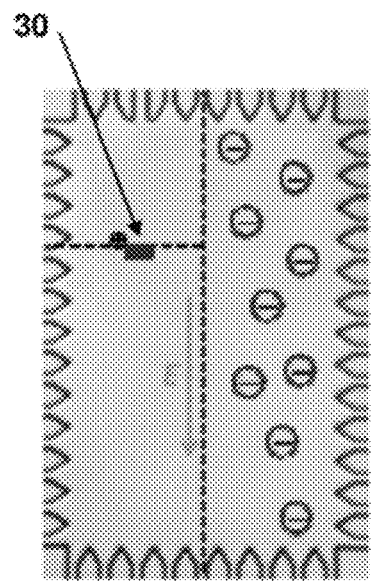
Figure 3C:
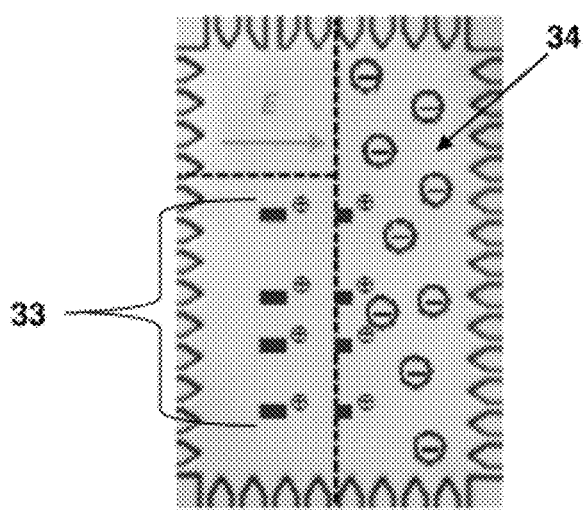
Figure 3D:
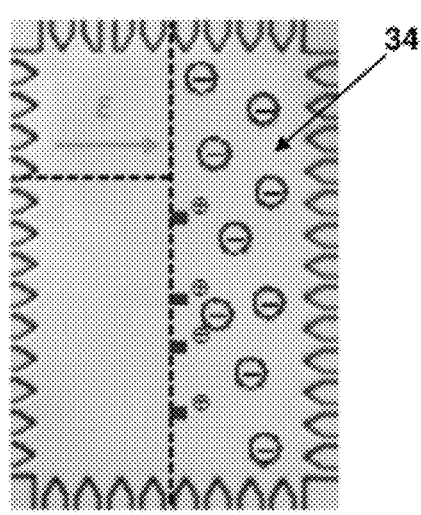

FIGS. 3A-3G show schematics of an embodiment of a method for detecting the presence of an analyte in a sample. The method includes polyacrylamide gel electrophoresis (PAGE) followed by post-separation sample transfer and, finally, detection using a labeled antibody probe. Analytes are electrokinetically transferred from a PAGE separation medium to a contiguous pan-capture binding medium and are identified in situ by specific affinity interactions. In step 1 (FIG. 3A), a sample 30 is contacted with the loading medium 31. The sample includes cetyltrimethylammonium bromide (CTAB), which binds to analytes (e.g., proteins) in the sample at an equal molar ratio to produce analytes with substantially the same charge-to-mass ratio. As such, a linear log-molecular mass (Mr) to mobility relation is observed for the separation of CTAB-treated proteins (see FIG. 7 (bottom)). In addition, CTAB-treated proteins have a positive charge, which may facilitate electrostatic binding of the proteins in the sample to the negatively charged pan-capture binding medium. After the sample 30 is contacted with the loading medium 31, an electric field is applied along the directional axis of the separation medium to direct the sample through the loading medium 31 to the interface between the loading medium 31 and the separation medium 32 (FIGS. 3A-3B). In step 2 (FIGS. 3B-3C), the various analytes in the sample are separated by electrophoresis through the separation medium 32. The separation medium 32 has a separation flow path with a first directional axis. An electric field is applied along the first directional axis (indicated by the vertical arrow) to direct the sample through the separation medium 32 (FIG. 3B). In step 3 (FIGS. 3C-3D), the separated analytes 33 can be transferred to the pan-capture binding medium 34 by applying an electric field along a second directional axis (indicated by the horizontal arrow) to direct the separated analytes 33 to the pan-capture binding medium 34 (FIG. 3C). The pan-capture binding medium includes an alkaline buffer (e.g., tricine-arginine buffer) and is negatively charged. The positively charged separated analytes electrostatically bind to the negatively charged binding medium (FIG. 3D). In step 4 (FIG. 3E), a blocking reagent (e.g., BSA) is contacted with the separated analytes bound to the binding medium. In some cases, the blocking reagent facilitates a minimization in non-specific binding of a labeled antibody to the separated analytes. After contacting the blocking reagent with the separated analytes, the blocking reagent may be washed away (FIG. 3F). In step 5 (FIG. 3G), a detectable label (e.g., a fluorescently labeled antibody) is contacted with the separated analytes bound to the binding medium. The detectable label specifically binds to the analyte of interest 35 (e.g., the target protein). Unbound label is washed away to facilitate a reduction in background signal (FIG. 3H). A positive detection of the detectable label indicates the presence of the analyte of interest 35 in the sample.

Systems

Aspects of certain embodiments include a system for detecting an analyte in a sample. In some instances, the system includes a microfluidic device as described herein. The system may also include a detector. In some cases, the detector is a detector configured to detect a detectable label. The detector may include any type of detector configured to detect the detectable label used in the assay. As described above, detectable label may be a fluorescent label, colorimetric label, chemiluminescent label, multicolor reagent, enzyme-linked reagent, avidin-streptavidin associated detection reagent, radiolabel, gold particle, magnetic label, etc. In some instances, the detectable label is a fluorescent label. In these instances, the detector may be configured to contact the fluorescent label with electromagnetic radiation (e.g., visible, UV, x-ray, etc.), which excites the fluorescent label and causes the fluorescent label to emit detectable electromagnetic radiation (e.g., visible light, etc.). The emitted electromagnetic radiation may be detected by the detector to determine the presence of the analyte bound to the binding medium.

In some instances, the detector may be configured to detect emissions from a fluorescent label, as described above. In certain cases, the detector includes a photomultiplier tube (PMT), a charge-coupled device (CCD), an intensified charge-coupled device (ICCD), a complementary metal-oxide-semiconductor (CMOS) sensor, a visual colorimetric readout, a photodiode, and the like.

Systems of the present disclosure may include various other components as desired. For example, the systems may include fluid handling components, such as microfluidic fluid handling components. The fluid handling components may be configured to direct one or more fluids through the microfluidic device. In some instances, the fluid handling components are configured to direct fluids, such as, but not limited to, sample solutions, buffers (e.g., electrophoresis buffers, wash buffers, release buffers, etc.), and the like. In certain embodiments, the microfluidic fluid handling components are configured to deliver a fluid to the separation medium of the microfluidic device, such that the fluid contacts the separation medium. The fluid handling components may include microfluidic pumps. In some cases, the microfluidic pumps are configured for pressure-driven microfluidic handling and routing of fluids through the microfluidic devices and systems disclosed herein. In certain instances, the microfluidic fluid handling components are configured to deliver small volumes of fluid, such as 1 mL or less, such as 500 µL or less, including 100 µL or less, for example 50 µL or less, or 25 µL or less, or 10 µL or less, or 5 µL or less, or 1 µL or less.

In certain embodiments, the systems include one or more electric field generators. An electric field generator may be configured to apply an electric field to various regions of the microfluidic device. The system may be configured to apply an electric field such that the sample is electrokinetically transported through the microfluidic device. For example, the electric field generator may be configured to apply an electric field to the separation medium. In some cases, the applied electric field may be aligned with the directional axis of the separation flow path of the separation medium. As such, the applied electric field may be configured to electrokinetically transport the analytes and components in a sample through the separation medium. In certain embodiments, the system includes an electric field generator configured to apply an electric field such that analytes and/or components in the sample are electrokinetically transported from the separation medium to the binding medium. For instance, an applied electric field may be aligned with the directional axis of the flow path of the binding medium. In some cases, the applied electric field is configured to electrokinetically transport selected analytes that have been separated by the separation medium. Analytes that have been separated by the separation medium may be transported to the binding medium by applying an appropriate electric field along the directional axis of the flow path of the binding medium. In some instances, the electric field generators are configured to apply an electric field with a strength ranging from 10 V/cm to 1000 V/cm, such as from 100 V/cm to 800 V/cm, including from 200 V/cm to 600 V/cm.

In certain embodiments, the electric field generators include voltage shaping components. In some cases, the voltage shaping components are configured to control the strength of the applied electric field, such that the applied electric field strength is substantially uniform across the separation medium and/or the binding medium. The voltage shaping components may facilitate an increase in the resolution of the analytes in the sample. For instance, the voltage shaping components may facilitate a reduction in non-uniform movement of the sample through the separation medium. In addition, the voltage shaping components may facilitate a minimization in the dispersion of the bands of analytes as the analytes traverses the separation medium.

In certain embodiments, the subject system is a biochip (e.g., a biosensor chip). By "biochip" or "biosensor chip" is meant a microfluidic system that includes a substrate surface which displays two or more distinct microfluidic devices on the substrate surface. In certain embodiments, the microfluidic system includes a substrate surface with an array of microfluidic devices.

An "array" includes any two-dimensional or substantially two-dimensional (as well as a three-dimensional) arrangement of addressable regions, e.g., spatially addressable regions. An array is "addressable" when it has multiple devices positioned at particular predetermined locations (e.g., "addresses") on the array. Array features (e.g., devices) may be separated by intervening spaces. Any given substrate may carry one, two, four or more arrays disposed on a front surface of the substrate. Depending upon the use, any or all of the arrays may be the same or different from one another and each may contain multiple distinct microfluidic devices. An array may contain one or more, including two or more, four or more, eight or more, 10 or more, 25 or more, 50 or more, or 100 or more microfluidic devices. In certain embodiments, the microfluidic devices can be arranged into an array with an area of 100 cm$^2$ or less, 50 cm$^2$ or less, or 25 cm$^2$ or less, 10 cm$^2$ or less, 5 cm$^2$ or less, such as 1 cm$^2$ or less, including 50 mm$^2$ or less, 20 mm$^2$ or less, such as 10 mm$^2$ or less, or even smaller. For example, microfluidic devices may have dimensions in the range of 10 mm×10 mm to 200 mm×200 mm, including dimensions of 100 mm×100 mm or less, such as 50 mm×50 mm or less, for instance 25 mm×25 mm or less, or 10 mm×10 mm or less, or 5 mm×5 mm or less, for instance, 1 mm×1 mm or less.

Arrays of microfluidic devices may be arranged for the multiplex analysis of samples. For example, multiple microfluidic devices may be arranged in series, such that a sample may be analyzed for the presence of several different analytes in a series of microfluidic devices. In certain embodiments, multiple microfluidic devices may be arranged in parallel, such that two or more samples may be analyzed at substantially the same time.

Aspects of the systems include that the microfluidic devices may be configured to consume a minimum amount of sample while still producing detectable results. For example, the system may be configured to use a sample volume of 100 μL or less, such as 75 μL or less, including 50 μL or less, or 25 μL or less, or 10 μL or less, for example, 5 μL or less, 2 μL or less, or 1 μL or less while still producing detectable results. In certain embodiments, the system is configured to have a detection sensitivity of 1 nM or less, such as 500 pM or less, including 100 pM or less, for instance, 1 pM or less, or 500 fM or less, or 250 fM or less, such as 100 fM or less, including 50 fM or less, or 25 fM or less, or 10 fM or less. In some instances, the system is configured to be able to detect analytes at a concentration of 1 μg/mL or less, such as 500 ng/mL or less, including 100 ng/mL or less, for example, 10 ng/mL or less, or 5 ng/mL or less, such as 1 ng/mL or less, or 0.1 ng/mL or less, or 0.01 ng/mL or less, including 1 pg/mL or less. In certain embodiments, the system has a dynamic range from $10^{-18}$ M to 10 M, such as from $10^{-15}$ M to $10^{-3}$ M, including from $10^{-12}$ M to $10^{-6}$ M.

In certain embodiments, the microfluidic devices are operated at a temperature ranging from 1° C. to 100° C., such as from 5° C. to 75° C., including from 10° C. or from 20° C. to 40° C. In some instances, the microfluidic devices are operated at a temperature ranging from 35° C. to 40° C.

Figure 5:
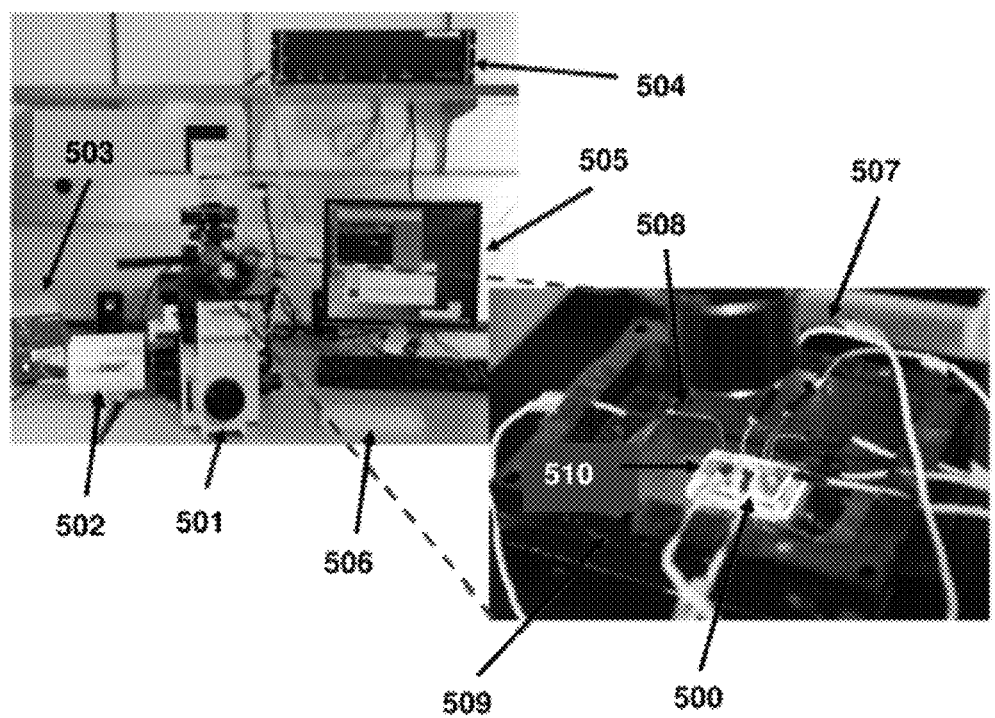
FIG. 5 shows a photograph and enlargement of a microfluidic system, according to embodiments of the present disclosure.

FIG. 5 shows a photograph and enlargement of a microfluidic system. In certain embodiments, the microfluidic system includes a microfluidic device 500 positioned in a fluorescence microscope 501. The fluorescence microscope 501 is operatively connected to a light source 503 and a detector 502. In some instances, the system includes a computer 505 configured to control the various components of the system when performing an assay. The computer 505 may also be configured to store and analyze data produced by the assay. In certain cases, the system includes an electric field generator 504, such as a high-voltage sequencer. The electric field generator 504 may be operatively connected to the microfluidic device 500 by leads 507 that include electrodes 508. The microfluidic device 500 may also a guide wire 509 for positioning the microfluidic device 500 in the fluorescence microscope 501. In addition, the microfluidic device 500 may be fluidically connected to a manifold 510 configured to direct a flow of a fluid (e.g., sample fluid, buffer, detectable label, reagent, etc.) to the microfluidic device 500. Samples, buffers, detectable labels, reagents, etc. may be contained in test tubes 506 for use in the assays.

Utility

The subject devices, systems and methods find use in a variety of different applications where determination of the presence or absence, and/or quantification of one or more analytes in a sample is desired. For example, the subject devices, systems and methods find use in the separation and detection of proteins, peptides, nucleic acids, and the like. In some cases, the subject devices, systems and methods find use in the separation and detection of proteins. In certain instances, the proteins are native proteins (e.g., non-denatured proteins). For instance, the microfluidic devices may include a separation medium configured to separate native proteins without denaturing the proteins. In some cases, the separation medium is configured to separate proteins under non-denaturing conditions, such as by using reagents, buffers, detergents, etc., that do not cause significant denaturing of the proteins in the sample. For example, the separation medium may include a non-denaturing detergent, such as, but not limited to, cetyltrimethylammonium bromide (CTAB). The use of non-denaturing conditions may simplify the overall separation and detection process by eliminating the need for renaturing the proteins in the sample.

In certain embodiments, the subject devices, systems and methods find use in the detection of nucleic acids, proteins, or other biomolecules in a sample. The methods may include the detection of a set of biomarkers, e.g., two or more distinct protein biomarkers, in a sample. For example, the methods may be used in the rapid, clinical detection of two or more disease biomarkers in a biological sample, e.g., as may be employed in the diagnosis of a disease condition in a subject, or in the ongoing management or treatment of a disease condition in a subject, etc. In addition, the subject devices, systems and methods may find use in protocols for the detection of an analyte in a sample, such as, but not limited to, Western blotting, Southern blotting, Northern blotting, Eastern, Far-Western blotting, Southwestern blotting, and the like.

In certain embodiments, the subject devices, systems and methods find use in detecting biomarkers. In some cases, the subject devices, systems and methods may be used to detect the presence or absence of particular biomarkers, as well as an increase or decrease in the concentration of particular biomarkers in blood, plasma, serum, or other bodily fluids or excretions, such as but not limited to urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue, and the like.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers may influence the choices of drug treatment or administration regimes given to an individual. In evaluating potential drug therapies, a biomarker may be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject devices, systems and methods. Furthermore, the early detection of biomarkers associated with diseases is facilitated by the high sensitivity of the subject devices and systems, as described above. Due to the capability of detecting multiple biomarkers on a single chip, combined with sensitivity, scalability, and ease of use, the presently disclosed microfluidic devices, systems and methods find use in portable and point-of-care or near-patient molecular diagnostics.

In certain embodiments, the subject devices, systems and methods find use in detecting biomarkers for a disease or disease state. In certain instances, the subject devices, systems and methods find use in detecting biomarkers for the characterization of cell signaling pathways and intracellular communication for drug discovery and vaccine development. For example, the subject devices, systems and methods may be used to detect and/or quantify the amount of biomarkers in diseased, healthy or benign samples. In certain embodiments, the subject devices, systems and methods find use in detecting biomarkers for an infectious disease or disease state. In some cases, the biomarkers can be molecular biomarkers, such as but not limited to proteins, nucleic acids, carbohydrates, small molecules, and the like.

The subject devices, systems and methods find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

The subject devices, systems and methods also find use in validation assays. For example, validation assays may be used to validate or confirm that a potential disease biomarker is a reliable indicator of the presence or absence of a disease across a variety of individuals. The short assay times for the subject devices, systems and methods may facilitate an increase in the throughput for screening a plurality of samples in a minimum amount of time.

In some instances, the subject devices, systems and methods can be used without requiring a laboratory setting for implementation. In comparison to the equivalent analytic research laboratory equipment, the subject devices and systems provide comparable analytic sensitivity in a portable, hand-held system. In some cases, the mass and operating cost are less than the typical stationary laboratory equipment. The subject systems and devices may be integrated into a single apparatus, such that all the steps of the assay, including separation, transfer, labeling and detecting of an analyte of interest, may be performed by a single apparatus. For example, in some instances, there are no separate apparatuses for separation, transfer, labeling and detecting of an analyte of interest. In addition, the subject systems and devices can be utilized in a home setting for over-the-counter home testing by a person without medical training to detect one or more analytes in samples. The subject systems and devices may also be utilized in a clinical setting, e.g., at the bedside, for rapid diagnosis or in a setting where stationary research laboratory equipment is not provided due to cost or other reasons.

Kits

Aspects of the present disclosure additionally include kits that have a microfluidic device as described in detail herein. The kits may further include a buffer. For instance, the kit may include a buffer, such as an electrophoresis buffer, a sample buffer, and the like. In certain cases, the buffer is an alkaline buffer, such as, but not limited to, a tricine-arginine buffer. In some instances, the buffer includes a detergent (such as SDS or CTAB), which is employed in the pan-capture of separated proteins, as described herein. For example, the buffer may include cetyltrimethylammonium bromide (CTAB).

The kits may further include additional reagents, such as but not limited to, release reagents, denaturing reagents, refolding reagents, detergents, detectable labels (e.g., fluorescent labels, colorimetric labels, chemiluminescent labels, multicolor reagents, enzyme-linked reagents, detection reagents (e.g., avidin-streptavidin associated detection reagents), calibration standards, radiolabels, gold particles, magnetic labels, etc.), and the like.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., diskette, CD, DVD, Blu-Ray, computer-readable memory, etc., on which the information has been recorded or stored. Yet another means that may be present is a website address which may be used via the Internet to access the information at a removed site. Any convenient means may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by mass, molecular mass is mass average molecular mass, temperature is in degrees Celsius, and pressure is at or near atmospheric.

EXAMPLES

Example 1

Design of Microfluidic Device

A glass microfluidic chip (10 mm×15 mm) (FIG. 1A) was designed using Autocad software (Autodesk, San Rafael; Calif.). A rectangular microfluidic chamber (1 mm×1.5 mm×0.02 mm) was designed to accommodate three functional gel regions for different Western blotting steps. FIG. 2 shows a schematic of the microfluidic chamber that included the loading gel for sample loading, the separation gel for protein sizing, and the blotting gel for transfer and target probing. The chamber was connected with several microfluidic channels, such as the injection channels and control channels. The width of each injection channel was 25 µm, and the width of each control channel was 10 µm. The injection channel was branched into three channels (see channels 1, 2, and 3 in FIG. 2) that formed a double-T junction, where a narrow sample plug was formed by applying a pinch current. Control channels (see channels 4, 5, 6, 7, and 8 in FIG. 2) were also linked to the chamber. Constant currents were applied via these resistive narrow channels from a current source. The electric fields were parallel to the currents. The fields were controlled to be parallel to the field from the injection channel that was used to transfer the sample plug into the chamber. Controlling the fields facilitated a minimization in sample dispersion in the chamber. Applying current in this manner facilitated transfer of the proteins horizontally and vertically while preserving the separation pattern.

Fabrication

To prepare the microfluidic chips, the glass microfluidic chips were lithographed, isotropically etched, and diced (Caliper Life Sciences, Hopkinton, Mass.). The etch depth was 20 µm. Eight access holes were drilled using glass drill bits. The chip was cleaned in a piranha bath and thermally bonded to a blank chip for 6 hours at 592° C. in a programmable oven.

Figure 6:
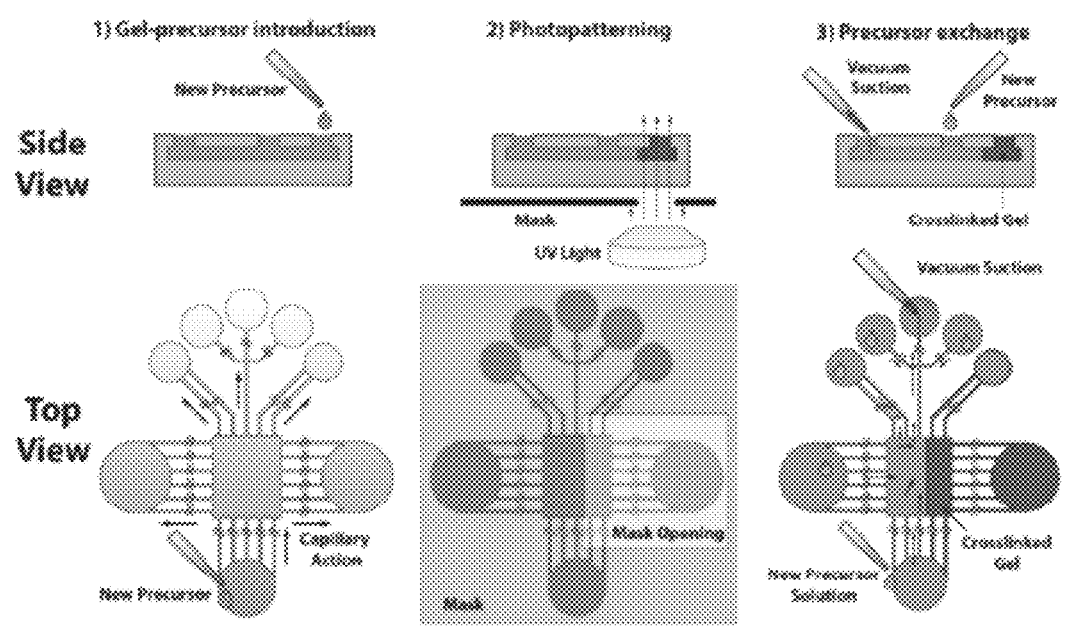
FIG. 6 shows schematics of the fabrication steps used for photo-patterning a polyacrylamide gel inside a microfluidic chamber, according to embodiments of the present disclosure.

Before photo-patterning of polyacrylamide (PA) gels inside the microfluidic chamber, the glass chip was cleaned by flushing the microfluidic channels with 0.1 M NaOH for 10 min, and rinsing with deionized (DI) water for 10 min and methanol for 5 min. For covalent linkage of the PA gel to the inner glass surface, a salination solution, 2:2:3:3 ratio of 3-(trimethoxysilyl)propyl methacrylate, glacial acetic acid, DI water, and methanol (all from Sigma, St. Luis, Mo.) was introduced into the chip and incubated for 30 min, and rinsed with methanol for 30 min. For photo-patterning of three functional gels, each gel precursor solution was introduced inside the chamber by capillary action, polymerized using UV light, and then evacuated and exchanged with subsequent precursor solution using vacuum suction. FIG. 6 shows a schematic drawing of the fabrication steps used for photo-patterning a polyacrylamide gel inside a microfluidic chamber. The 9% T (T=total acrylamide content) precursor solution for the binding medium gel was prepared using 30 µL of 30% T acrylamide/bisacrylamide (Sigma), 10 µL of 1 mg/mL streptavidin acrylamide (Invitrogen, Carlsbad, Calif.), 40 µL of 2 mg/mL of the binding member (e.g., capture protein), 5×TA buffer (1×TA: 25 mM tricine-14 mM arginine, all from Sigma), and 5 µL of 1% (v/w) photoinitiator VA-086 solution (Wako Chemical, Richmond, Va.). The 6% T separation gel and 3% T loading gel were photo-patterned similarly except that streptavidin-acrylamide and the binding member (e.g., capture protein) were not included in polyacrylamide gel precursors. 3% T gel was also polymerized in the microfluidic injection channels for later sample loading.

A UV exposure system was used for photo-patterning. An inverted microscope (IX-50, Olympus, Melville, N.Y.) equipped with mercury-lamp and UV objective lens (UP-LANS-APO 4×, Olympus) allowed for manual alignment between a glass chip and a transparency mask (Fineline-Imaging, Colorado Springs, Colo.) and UV exposure. The binding and separation gels were exposed for 8 min at 13 mW/cm$^2$. The loading gel was blanket-exposed for 6 min at 9 mW/cm$^2$ under a UV lamp (Blak-Ray, Upland, Calif.).

Four molecular mass standards were conjugated with fluorescein (Alexa Fluor 488, Invitrogen): 800 nM protein G (20 kDa, Abcam, Cambridge, Mass.), 200 nM ovalbumin (OVA, 45 kDa, Sigma), 200 nM bovine serum albumin (BSA, 68 kDa, Sigma), and 500 nM α-actinin (95 kDa, Sigma). The proteins were solubilized in 1×TA buffer. 0.1% CTAB (Sigma) was added to the proteins 5 min before loading to the chip.

Microfluidic PAGE Assay

All assay steps of microchip Western blotting (see FIGS. 3A-3G) were performed by controlling voltage and current via the eight access ports (see FIG. 2) with a high-voltage sequencer (Caliper Life Sciences). The voltage/current sequence is shown in Table 1.

TABLE 1

Voltage/Current Program for Western Blotting Assay Steps

| Assay steps | access port # | | | | | | | |
|---|---|---|---|---|---|---|---|---|
| | 1 | 2 | 3 | 4 | 5 | 6 | 7 | 8 |
| Plug formation | −261 V | −350 V | −200 V | 0 A | 0 A | 0 A | 0 A | −267 V |
| Sample loading/Separation | −200 V | −320 V | −320 V | −270 V | −270 V | 0 A | 0 A | −400 V |
| Electrotransfer | 0 A | 0 A | 0 A | 0 A | 0 A | −200 V | −100 V | 0 A |
| Blocking/Immunodetection | 0 A | 0 A | 0 A | 0 A | 0 A | −200 V | −300 V | 0 A |

Figure 4:
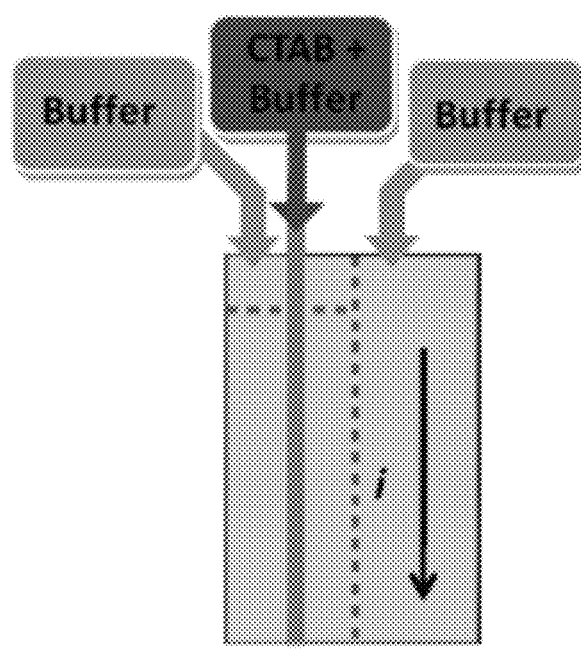
FIG. 4 shows a schematic of the addition of a stream of CTAB buffer into the separation medium by electrophoretic injection, which defines the separation axis in the microfluidic device, according to embodiments of the present disclosure.

Prior to the sample loading step, CTAB was electrophoretically introduced in PA gels (see FIG. 4). Pre-treating the PA gels with CTAB may facilitate separation of the analytes in the sample because without sufficient CTAB concentration in the gels: (1) protein may lose CTAB ions that were previously bound in the sample preparation step due to dilution, and (2) electrostatic interaction between negatively charged PA gel and positively charged CTAB-treated protein may result in binding of proteins before the PAGE separation. Therefore, 0.1% CTAB was injected into microchannels from the access ports 1, 2 and 3 for 10 min, and injected into the microfluidic chamber for 5 min as a narrow band that was wide enough for a protein plug to migrate without non-specific interaction.

An epi fluorescence microscope (IX-7, Olympus) equipped with Peltier-cooled CCD camera (CoolSNAP HQ2, Photometrics, Tucson, Ariz.) was used to capture fluorescence images of proteins during all assay stages. The images were later analyzed for protein quantitation using ImageJ software (NIH, Bethesda, Md.).

Results

Figure 7:
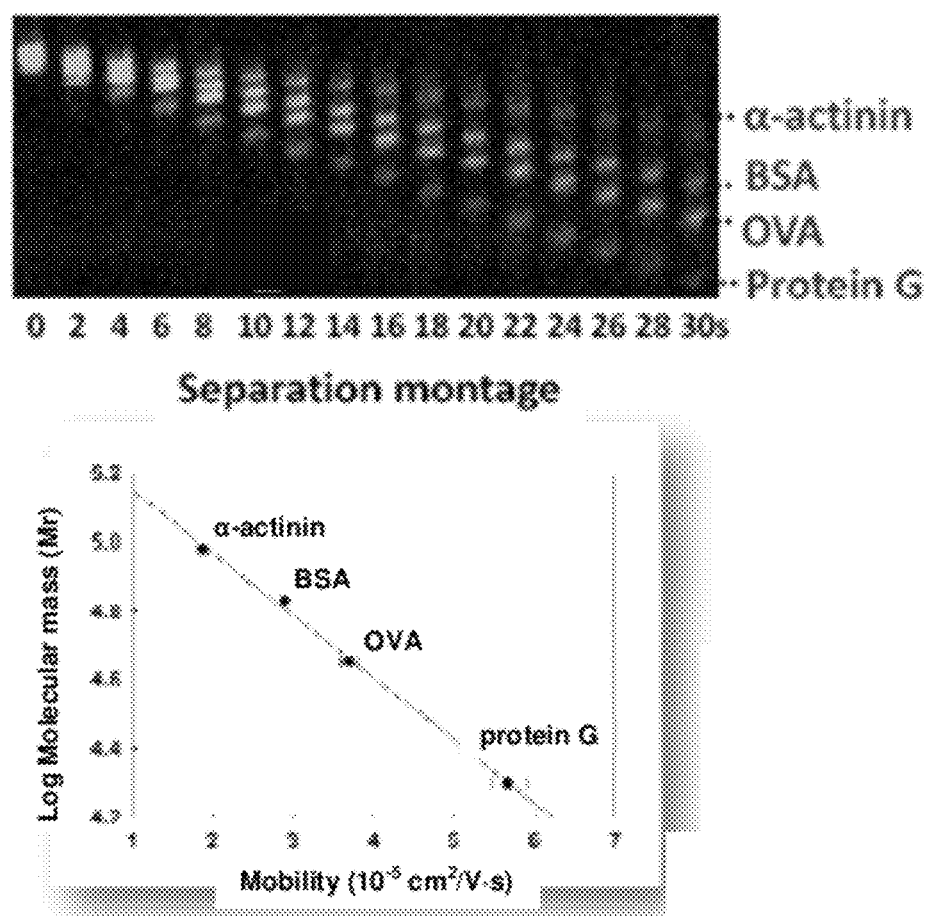
FIG. 7 (top) shows a montage of fluorescence images over time (seconds) for the separation of a protein sample in a microfluidic device, according to embodiments of the present disclosure.

The CTAB-treated molecular-mass standard was pipetted into the access hole 3. A narrow plug was formed at the double-T junction. Due to large pore size (3% T) sample loading in the loading gel required 1 min or less. The sample was injected into the microfluidic chamber (FIG. 3A). Upon reaching the separation gel (6% T), the decrease in pore size resulted in sample stacking at the loading gel-separation gel interface (FIG. 3B). While migrating downstream, the protein mixture separated into multiple bands based on the molecular mass of the proteins due to sieving action in the PA gel (FIG. 3C). As seen in FIG. 7, top, a protein sample that included α-actinin, BSA, OVA and protein G stacked and then separated into compact bands within 30 s. A linear log-molecular mass (log-Mr) vs. mobility ($10^{-5}$ $cm^2/V \cdot s$) relation was observed (see FIG. 7, bottom), indicating that Mr determination using CTAB-PAGE was accurate.

Figures 8A, 8B, 8C:
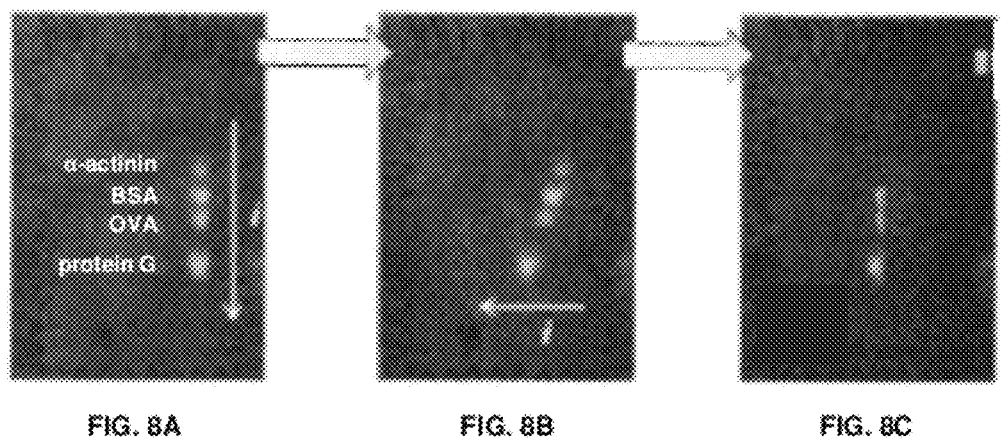
FIGS. 8A-8C show fluorescence images of the separation and transfer of four proteins (protein G, OVA, BSA, and α-actinin) in a sample using a microfluidic device, according to embodiments of the present disclosure.

After separation, a horizontal electric field was applied to transfer the separated protein bands to the binding gel (FIGS. 3C-3D). Upon reaching the binding gel, the separated protein bands were compressed and immobilized due to electrostatic interaction with PA gel (FIG. 3D). FIGS. 7A, 7B and 7C show fluorescence images of the separation and transfer of four proteins (protein G, OVA, BSA, and α-actinin) in a sample. FIG. 8A shows a fluorescence image of the separation of the four proteins into distinct bands in the separation gel. FIG. 8B shows a fluorescence image of the transfer of the separated proteins from the separation gel to the binding medium. FIG. 8C shows a fluorescence image of the binding of the separated proteins to the binding medium.

In alkaline tricine-arginine (TA) buffer (pH 8.2), PA was hydrolyzed and had a net negative charge. When biotinylated binding members of large Mr and low-pI point such as IgG (pI=5.5-8.0, Mr=150 kDa) and β-galactosidase (pI=4.61, Mr=465 kDa) were copolymerized in the PA gel using a streptavidin-acrylamide linker, the charge density was increased, which was evidenced by a stronger immobilization of the sample proteins. Electrotransfer was completed in about 42 s. Based on fluorescent intensity, significantly detectable amounts of separated proteins were retained. Retention of separated proteins after the immobilization was 75%, 77%, 65%, and 78% for protein G, OVA, BSA, and α-actinin, respectively. The near 1:1 correlation between separation pattern and immobilization was noted (e.g., separation resolution between protein G and OVA was 1.41 before and after the blotting), indicating that protein transport was efficient.

Figure 9A:
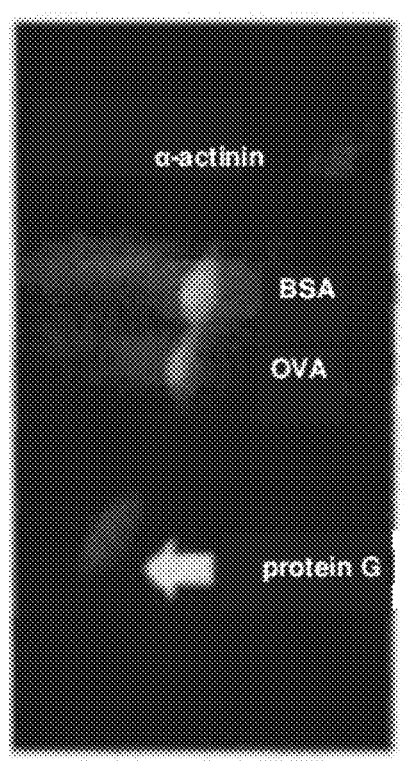
FIG. 9A shows a fluorescence image of separated proteins in a sample (protein G, OVA, BSA, and α-actinin) immobilized in the binding medium of a microfluidic device, according to embodiments of the present disclosure.
Figure 9B:
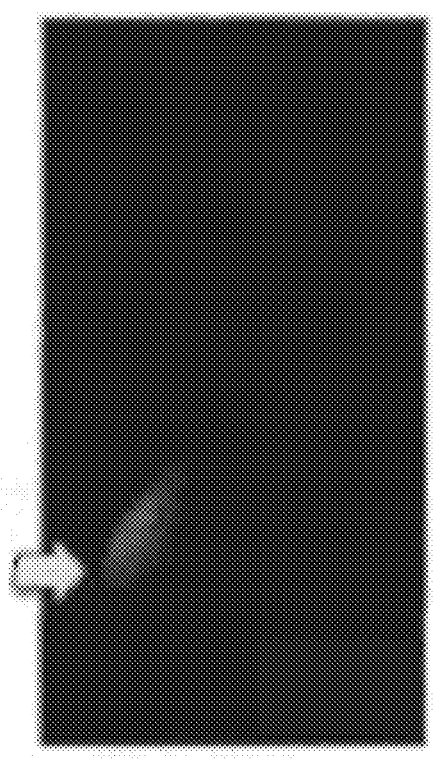
FIG. 9B shows a fluorescence image of subsequent binding of a detectable label (antibody) to protein G in the separated sample, according to embodiments of the present disclosure.

Assay from sample loading to electrotransfer was completed in about 63 s, which was approximately 10-fold less time than a conventional Western blotting assay. After immobilization, horizontal electric field was continuously applied to wash off residual CTAB from the binding gel. Washing off residual CTAB may facilitate subsequent probing antibody introduction because the probing antibody may precipitate when exposed to CTAB. FIG. 9A shows a fluorescence image of the proteins (protein G, OVA, BSA, and α-actinin) immobilized in the binding medium. In the following blocking step, open charge sites on the gel were blocked by electrophoretically introducing 1% BSA solubilized in TA buffer to prevent non-specific antibody binding (FIG. 3E). Residual BSA was washed off by applying a reverse electric field (FIG. 3F). After the blocking, an antibody probe conjugated with Alexa Fluor 568 (Invitrogen) was introduced and incubated for 10 min (FIG. 3G). The antibody probe was washed off by applying a reverse field (FIG. 3H). The immunoaffinity probe bound specifically to the immobilized target, as shown in FIG. 9B. 800 nM of protein G was detected without the need for a protein-renaturing step, which is typically required for conventional Western blotting using SDS-PAGE gel electrophoresis.

Conclusion Microfluidic devices as disclosed herein allowed for device miniaturization and automation of the assay by using multi-channel voltage/current control. In addition, the microfluidic assay performance was also significantly better than typical SDS-PAGE Western blotting assays, with the microfluidic assay having sample consumption reduced by about 100-1000 times (e.g., about 10 ng) and rapid completion times (about 2.5 hours vs. 1-2 days). The electrostatic interaction between the sample analytes and the binding medium allowed for the electrotransfer of all resolved protein to the binding medium. In certain embodiments, copolymerization of matched-pair antibodies with the binding medium to immobilize the separated protein targets was not required. Instead, immunoaffinity probes were introduced after the separated were electrostatically immobilized in the binding medium. In some cases, electrostatic immobilization of the separated proteins facilitated detection of the separated proteins through the use of enzyme-linked secondary antibodies, which may be specifically bound to the primary antibody bound to the analyte of interest. Secondary detection antibodies may facilitate an increase in detectable signal, which may allow for an increase in in the detection limit and label-free detection. In addition, embodiments of the present disclosure that use CTAB-PAGE may facilitate immunoblotting without complex and time-consuming protein renaturation.

Example 2

Figures 10A, 10B, 10C, 10D:
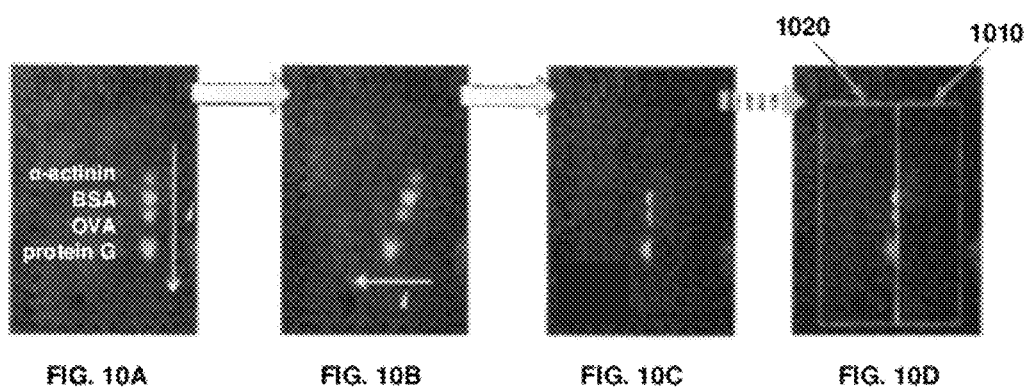
FIGS. 10A-10D show fluorescence images of separated proteins in a sample (protein G, OVA, BSA, and α-actinin) during separation and binding in a microfluidic device that included immunoglobulin G (IgG) in the binding medium, according to embodiments of the present disclosure.

Experiments were performed using the same experimental protocol as Example 1 to determine the transfer efficiency and reproducibility of the assay. The binding member (e.g., capture protein) used in the fabrication of the binding medium of the microfluidic device was 150 kDa IgG (anti-C-reactive protein). A sample containing protein G (20 kDa), OVA (45 kDa), BSA (68 kDa), and α-actinin (95 kDa) was separated in the separation medium and transferred to the binding medium. The separation step was completed in 21 sec after loading the sample (FIG. 10A). FIG. 10B shows a fluorescence image during the transfer of the separated sample 35 s after sample loading. Transfer of the separated sample from the separation medium 1010 to the binding medium 1020 was completed in 42 sec (e.g., 63 sec after sample loading) (FIG. 10C). Proteins were retained by the binding medium 1020 even after washing the bound proteins with buffer, as shown in the fluorescence image in FIG. 10D, taken 139 s after sample loading. Table 2 shows the separation resolution (SR) of the proteins in the sample during the transfer step (FIG. 10B) and after binding to the binding medium (FIG. 10C). As shown in Table 2, the proteins maintained their separation resolution during the transfer and binding steps. Table 3 shows the capture efficiency (%) for the proteins in the sample after binding to the binding medium (FIG. 10C) and after the buffer wash (FIG. 10D). As shown in Table 3, the binding medium retained detectable amounts of each protein during the assay.

TABLE 2

| Separation Resolution | | | |
| --- | --- | --- | --- |
| Assay Step | Protein G - OVA | OVA - BSA | BSA - α-actinin |
| Transfer | 1.41 | 0.90 | 1.32 |
| Binding | 1.41 | 0.97 | 1.76 |

TABLE 3

| Capture Efficiency (%) | | | | |
| --- | --- | --- | --- | --- |
| Assay Step | Protein G | OVA | BSA | α-actinin |
| Binding | 75 | 77 | 65 | 78 |
| Buffer Wash | 52 | 57 | 49 | 25 |

Example 3

Figure 11A:
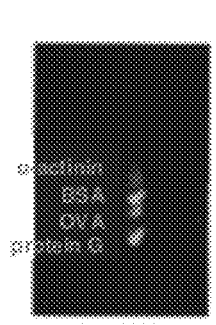
FIGS. 11A-11D show fluorescence images of separated proteins in a sample (protein G, OVA, BSA, and α-actinin) during separation and binding in a microfluidic device that included β-galactosidase (β-gal) in the binding medium, according to embodiments of the present disclosure.
Figure 11B:
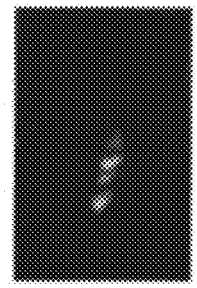
Figure 11C:
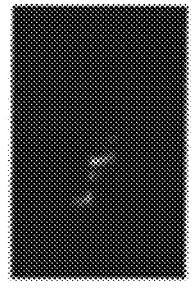
Figure 11D:
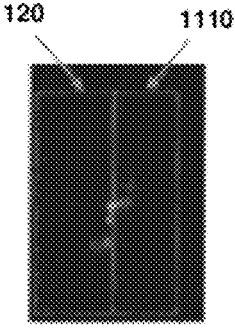

Experiments were performed using the same experimental protocol as Example 1 to determine the transfer efficiency and reproducibility of the assay. The binding member (e.g., capture protein) used in the fabrication of the binding medium of the microfluidic device was 465 kDa β-galactosidase (pI=4.61). A sample containing protein G (20 kDa), OVA (45 kDa), BSA (68 kDa), and α-actinin (95 kDa) was separated in the separation medium and transferred to the binding medium. The separation step was completed in 18 sec after loading the sample (FIG. 11A). FIG. 11B shows a fluorescence image during the transfer of the separated sample 21 s after sample loading. Transfer of the separated sample from the separation medium 1110 to the binding medium 1120 was completed in 20 sec (e.g., 38 sec after sample loading) (FIG. 11C). Proteins were retained by the binding medium 1120 even after washing the bound proteins with buffer, as shown in the fluorescence image in FIG. 11D, taken 53 s after sample loading. Table 4 shows the separation resolution (SR) of the proteins in the sample during the transfer step (FIG. 11B) and after binding to the binding medium (FIG. 11C). As shown in Table 4, the proteins maintained their separation resolution during the transfer and binding steps. Table 5 shows the capture efficiency (%) for the proteins in the sample after binding to the binding medium (FIG. 11C) and after the buffer wash (FIG. 11D). As shown in Table 5, the binding medium retained detectable amounts of each protein during the assay.

TABLE 3

| Separation Resolution | | | |
| --- | --- | --- | --- |
| Assay Step | Protein G - OVA | OVA - BSA | BSA - α-actinin |
| Transfer | 1.60 | 0.89 | 1.01 |
| Binding | 1.55 | 0.86 | 1.05 |

TABLE 4

| Capture Efficiency (%) | | | | |
| --- | --- | --- | --- | --- |
| Assay Step | Protein G | OVA | BSA | α-actinin |
| Binding | 71 | 79 | 62 | — |
| Buffer Wash | 45 | 42 | 45 | 27 |

Example 4

Fabrication of Microfluidic Device

A glass microfluidic chip was designed using AUTOCAD software (Autodesk, San Rafael, Calif.), and micromachined (Caliper Life Sciences, Hopkinton, Mass.). The width of the injection channel was 25 μm, and the width of control channels was 10 μm. The size of the central microfluidic chamber was 1.0 mm×1.5 mm (FIGS. 1A-1B). Eight access ports were drilled and the chip was thermally bonded to a blank chip in a programmable oven. The completed glass chip is shown in FIG. 1A. The interior of a glass chip was thoroughly cleaned before gel polymerization using 0.1 M NaOH (10 min), DI water (10 min), and methanol (5 min). The inner glass surface was functionalized for covalent linkage to PA (polyacrylamide) gel using silane solution that included a 2:2:3:3 ratio of 3-(trimethoxysilyl) propyl methacrylate, glacial acetic acid, DI water, and methanol (all from Sigma, St. Luis, Mo.). Gel precursor solution was introduced inside the glass chip by capillary action (FIG. 6, Step 1). The electrostatic binding medium was prepared by copolymerizing β-gal (β-galactosidase, tetramer, 465 kDa) with acrylamide using streptavidin-biotin linker. The precursor composition was 6-9% T w/v acrylamide/bisacrylamide (Sigma), 3.8 μM of streptavidin acrylamide (Invitrogen, Carlsbad, Calif.), 0-1.6 μM of biotinylated n-gal from *E. coli* (Sigma), and 0.1% w/v photoinitiator VA-086 solution (Wako Chemical, Richmond, Va.) in 1×TA (tricine-arginine) buffer (Sigma). The PA precursor composition was polymerized using an inverted microscope (IX-70, Olympus, Center Valley, Pa.), UV light source, and a photolithography mask (FIG. 6, Step 2). Un-polymerized precursor composition was evacuated and exchanged with subsequent precursor using vacuum suction (FIG. 6, Step 3). After gel fabrication was completed, the chip was stored in 1×TA buffer until use. The microfluidic device was reusable; after the assay was completed, the microfluidic chips were recycled by removing PA gels in heated 2:1 perchloric acid and hydrogen peroxide bath.

Assay Steps

The method includes five assay steps: 1) sample loading; 2) CTAB-PAGE for protein separation and sizing; 3) electrotransfer and electrostatic pan-capture of the separated proteins by the electrostatic binding medium (EBM); 4) blocking of non-specific binding sites in EBM; and 5) antibody-based probing of the immobilized protein bands. The assay may be automated, and the voltage and current sequence of the assay steps for the microfluidic system is shown in Table 5, below.

complexes migrated from the anode to the cathode. The discontinuous 3 to 6% T gel interface between the loading medium and the separation medium reduced the injected protein sample plug width, defined as $\pm 2\sigma$ of a Gaussian fit, by 57% (i.e., 493 to 213 µm).

During Step 2), CTAB-PAGE was used to separate the proteins and obtain protein size information. Under an applied electric field (47 V/cm), intermediate to small Mr species were fully resolved (e.g., SR>1.5 for the least resolved BSA-OVA peaks) after an elapsed separation time of 36 s. Sizing was completed in a separation distance of 1496 µm (defined as the fastest peak position when the least resolved peak pair is at SR=1.5). CTAB-PAGE analysis of a Mr standard ladder (20 to 118 kDa: 200 nM each of protein G,

TABLE 5

Voltage and Current Sequence

| Assay steps | access port # | | | | | | | |
|---|---|---|---|---|---|---|---|---|
| | 1 | 2 | 3 | 4 | 5 | 6 | 7 | 8 |
| 1) Sample loading | −261 V | −350 V | −200 V | 0 A | 0 A | 0 A | 0 A | −267 V |
| 2) Separation | −200 V | −320 V | −320 V | −270 V | −270 V | 0 A | 0 A | −400 V |
| 3) Electrotransfer | 0 A | 0 A | 0 A | 0 A | 0 A | −200 V | −100 V | 0 A |
| 3) Residual CTAB wash | 0 A | 0 A | 0 A | 0 A | 0 A | −200 V | −100 V | 0 A |
| 4) Blocking buffer injection | 0 A | 0 A | 0 A | 0 A | 0 A | −200 V | −300 V | 0 A |
| 4) Residual blocking buffer wash | 0 A | 0 A | 0 A | 0 A | 0 A | −200 V | −100 V | 0 A |
| 5) Antibody probe injection | 0 A | 0 A | 0 A | 0 A | 0 A | −200 V | −300 V | 0 A |
| 5) Residual antibody wash | 0 A | 0 A | 0 A | 0 A | 0 A | −200 V | −100 V | 0 A |

A separation medium of 6% T PA gel was photopolymerized in the central chamber (FIG. 2) and defined the separation axis. The relatively larger pore-size loading gel (3% T) allowed efficient protein loading, and the larger-to-smaller pore-size at the interface between the loading medium (3% T) and the separation medium (6% T) minimized injection dispersion by "stacking" the sample proteins. The run buffer along the separation axis was defined by electrophoretically injecting a stream of CTAB prior to protein injection (FIG. 4). CTAB detergent was included in the buffer of the loading medium and separation medium. CTAB was added to the buffer in situ. CTAB of 0.1-0.5% was loaded to injection channels #1-3 (see FIG. 2) and electrophoretically introduced into microchannels for 10 min. Then, CTAB was injected to the separation medium as a narrow band (FIG. 4) for 10 min before the sample loading. This injection defined the separation axis with minimal protein band dispersion. Protein G (PG, 20 kDa), OVA (45 kDa), BSA (68 kDa), (all from Invitrogen), and phosphorylase b (97.2 kDa), α-actinin (αA, 95 kDa), β-gal* (β-galactosidase monomer, 116 kDa), (all from Sigma), and S100B (10.5 kDa) and lactoferrin (LF, 78 kDa), (all from Abcam, Cambridge, Mass.), were either conjugated as manufactured or conjugated before use with Alexa Fluor 488 (Invitrogen) following manufacturer's instruction. Anti-rabbit polyclonal-PG (Abcam) was conjugated with Alexa Fluor 568 (Invitrogen). The proteins and antibodies were all solubilized in 1×TA buffer. Before the assay began, protein sample was diluted in sample buffer (1×TA: 25 mM tricine+ 14 mM arginine+0.1% w/v CTAB) 15 min before the assay and then electrophoretically loaded to the loading medium.

In Step 1) of the assay, a protein sample that included 6-gal* (* indicates 6-gal monomer, not "β-gal", the tetramer used for protein capture in the EBM), BSA, OVA and protein G was injected along the separation axis. In contrast to a typical SDS-PAGE system, positively charged CTAB-protein OVA, BSA and α-actinin) yielded a log-linear Mr to mobility relation ($y = -1.96 \times 10^3 x + 5.33$, $R^2 = 0.997$, n=5; see FIG. 7 (bottom)).

The molecular mass of unknown species was also accurately predicted using CTAB-PAGE. Using a log-linear Mr to mobility curve, Mr of lactoferrin (LF, 78 kDa) was estimated within 1.1% error. Five ladder proteins, S100B, OVA, BSA, phosphorylase b, and β-gal*, were used to yield a log-linear Mr to mobility relation. LF protein (78 kDa) co-migrated with the ladder, and Mr of the LF was calculated using mobility data and the log-linear Mr to mobility calibration curve. The predicted Mr was 78.8 kDa (1.05% error).

Step 3) included transfer and binding, which included electrophoretic transfer of the separated proteins and pan-protein capture on the electrostatic binding medium (EBM). The electrostatic capture was non-specific, meaning that all CTAB-protein complexes were immobilized on the binding medium. Detectable labels (e.g., detection antibodies) in free solution were introduced to the binding medium after electrotransfer. No matched antibody pair was needed in the binding medium. To fabricate the EBM, β-galactosidase (β-gal) was copolymerized in a 9% T PA gel as the anionic moiety. β-gal had a high negative surface charge resulting from a low p/point (4.61) and large Mr (465 kDa). The total number of negative surface charges on wild type β-gal from *E. coli* was significant (−160, pH 8.2). Copolymerization of β-gal at 1.6 µM with the PA binding medium yielded a stationary, charge-bearing region contiguous with the separation medium.

Figure 12:
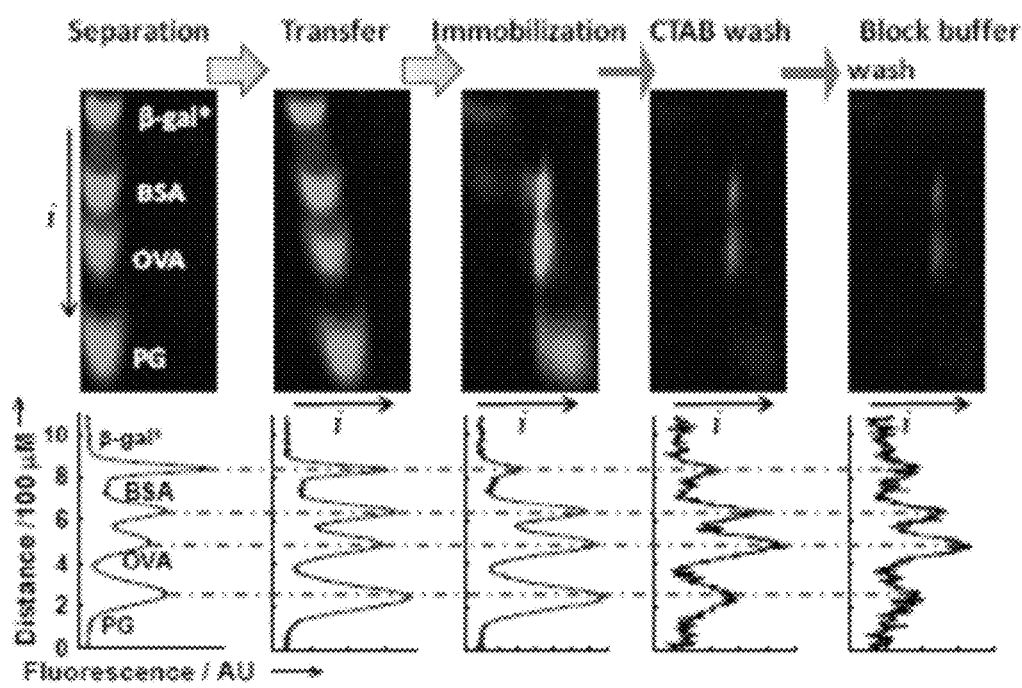
FIG. 12 shows fluorescence images and corresponding graphs of fluorescence intensity for various steps including the separation, transfer, binding (e.g., immobilization), washing and blocking performed during a method, according to embodiments of the present disclosure.

As shown in FIG. 12, resolved proteins were electrotransferred from the separation axis to the EBM. Electrotransfer was completed in 31 s by applying a transverse electric field. Electrostatic attraction to the EBM bound the CTAB-protein complexes to the binding medium and yielded immobilization of the proteins. In addition, protein bands migrating into the EBM were enriched by being horizontally compressed (25%, 56% and 65% peak-width reduction for PG, OVA and BSA, respectively). As determined by comparing the AUC (area under the curve) before transfer to that on the EBM, material retention was 92%, 100%, 66% and 21% for PG, OVA, BSA and β-gal*, respectively at 31 s. PA gel hydrolyzes and bears net negative charges in alkaline media. Positively charged CTAB-protein complexes bind to the negatively charged binding medium. Sample proteins were immobilized on the binding medium without loss of separation information, which facilitated subsequent identification of the separated proteins. Throughout Steps 4) and 5) after electrotransfer, sizing information was retained as shown in the corresponding fluorescence intensity graphs in FIG. 12. Comparison of separation resolution (SR) on the separation axis to that on the EBM shows that the separation of the sample proteins was retained during electrotransfer and binding (see Table 6). Table 6 shows separation resolution between two neighboring protein peaks during microfluidic assay steps. Separation resolution was calculated using the equation: $SR=(X_2-X_1)/(w_2+w_1)$, where $X_1$, $X_2$ are the center of two neighboring peaks and $w_1$, $w_2$ are their peak widths (2 times of variance of Gaussian fit). The peak width and center were estimated using nonlinear Gaussian curve fitting (OriginLab, Northampton, Mass.).

TABLE 6

Separation Resolution (SR) and Percent Variation (% V)

| | Neighboring Protein Bands | | | | | |
| --- | --- | --- | --- | --- | --- | --- |
| | protein G - OVA | | OVA - BSA | | BSA - β-gal* | |
| Assay Step | SR | % V | SR | % V | SR | % V |
| Separation | 1.38 | — | 0.92 | — | 1.52 | — |
| Transfer | 1.36 | 1.47 | 0.96 | 4.17 | 1.69 | 10.0 |
| Binding | 1.32 | 4.55 | 0.95 | 3.16 | 1.52 | 0 |
| Washing | 1.37 | 0.73 | 1.00 | 8 | 1.84 | 17.4 |
| Blocking | 1.31 | 5.34 | 1.02 | 9.80 | 1.50 | 1.33 |

Figure 13:
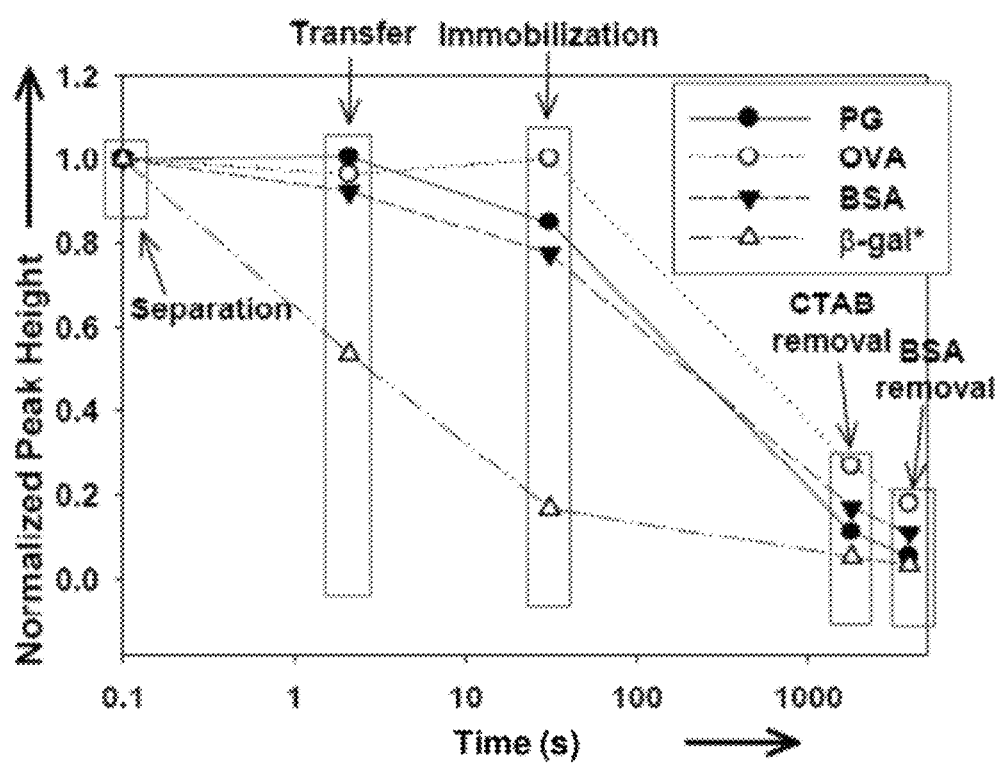
FIG. 13 shows a graph of protein capture efficiency for various steps including the separation, transfer, binding (e.g., immobilization), washing and blocking performed during a method, according to embodiments of the present disclosure.

Step 4) of the assay was an EBM blocking step that contacted the charge sites of the PA binding medium with BSA to minimize non-specific binding of antibody probe in subsequent Step 5). Prior to blocking, residual and free CTAB was electrophoretically washed from the EBM by applying a lateral electric field for 30 min (E=45 V/cm). The washing step minimized background signal that may be due to antibody association with CTAB. During the washing step, protein capture was 11%, 29%, 13% and 5% for PG, OVA, BSA and β-gal*, respectively. For the blocking step, 1% BSA w/v was electrophoretically contacted to the EBM using reverse polarity (e.g., BSA was negatively charged in non-detergent condition). After a 10 min blocking incubation, a reverse field was applied for 15 min to remove unbound blocking BSA. Following the blocking step, immobilized protein signal was 6%, 19%, 8% and 5% for PG, OVA, BSA and β-gal*, respectively. After the final blocking-BSA wash, protein capture reached a steady state. FIG. 13 shows a graph of fluorescence intensity (normalized peak height), representing material retention of protein bands, over time (seconds). The fluorescence intensity decreased exponentially as a function of time in the semi-log plot (the time axis was shifted 0.1 s because of the logarithmic time scale). In FIG. 13, no further significant reduction was observed after the washing step to remove unbound blocking BSA.

Figure 14:
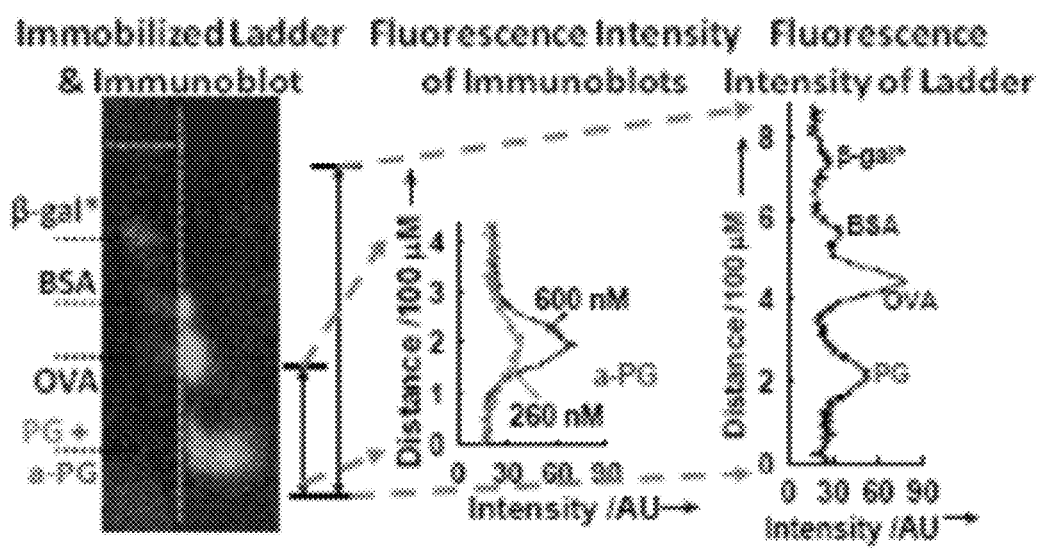
FIG. 14 shows a multispectral composite fluorescence image of separated sample proteins (protein G, OVA, BSA, and β3-gal* (β-galactosidase monomer)) with protein G labeled with a detectable label (e.g., antibody probe), according to embodiments of the present disclosure.

In Step 5), antibody probing of the immobilized and blocked separated proteins on the EBM was performed. Antibody probe conjugated with red fluorophore (Alexa Fluor 568) was electrophoretically introduced to the EBM, incubated for 10 min, and unbound antibody was electrophoretically washed away. FIG. 14 shows a multispectral fluorescence image of probing results for 200 nM rabbit polyclonal antibody binding to an immobilized protein G (PG) target. Fluorescence signal from the probing antibody was specific for PG with a low background (SNR of 34, based on AUC) 11 min after the antibody washing step. The signal-to-noise ratio (SNR) of immobilized proteins was still detectable after two hours of electric field application: 6, 16, 8 and 5 for PG, OVA, BSA and β-gal*, respectively. Antibody probing of PG at two concentrations (600 nM vs. 260 nM) resulted in corresponding probing antibody signals of 1278 vs. 637, respectively. The direct correlation between concentration and signal may facilitate development of a calibration curve, thus allowing absolute protein quantitation. Antibody probing did not include a separate protein renaturing step required for conventional SDS Western blotting. Compared with conventional Western blotting, assay durations were reduced about over 100× from protein loading to electrotransfer (about 3 min vs. 4-5 h), and 10 to 20× for the complete assay (e.g., about 2 h vs. 1-2 days). Sample consumption was also reduced over 100× (e.g., about 10 ng vs. 1-40 µg).

Example 5

Figure 15A:
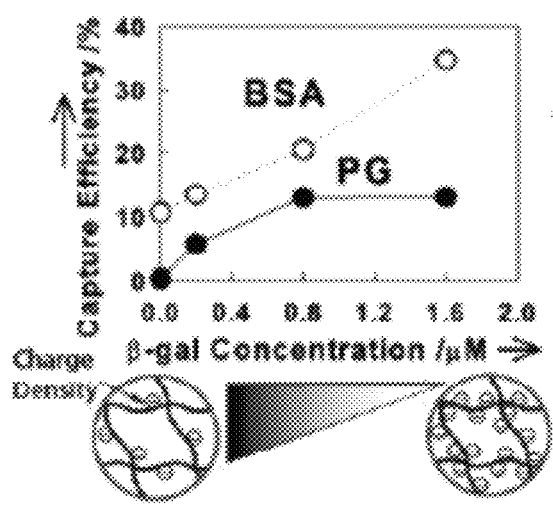
FIG. 15A shows a graph of capture efficiency (%) vs. β-gal concentration (μM) illustrating the effect of charge density of the electrostatic binding medium, according to embodiments of the present disclosure.

Additional experiments were performed to characterize protein capture on the EBM. Two physicochemical EBM properties were studied: the charge density of capture sites on the EBM and the ionic strength of the transfer buffer (see FIGS. 15A-15B). As a test sample, PG and BSA (+0.1% CTAB) were injected, separated, and immobilized in the EBM. Similar to electrotransfer characterization done in Step 3) of Example 4 discussed above, the capture efficiency was obtained based on material retention after 30 min of electric field application for the CTAB washing in Step 4) of Example 4. To study the effect of varying the charge density, microfluidic devices having an EBM with an increasing immobilized n-gal concentration (0 µM, 0.2 µM, 0.8 µM, 1.6 µM) were fabricated (FIG. 15A and FIG. 16). FIG. 16 shows fluorescence images of experiments studying the binding strength of proteins in different charge densities. Protein G and BSA migrated as bands in the separation medium 1610. After a transverse electric field was applied, protein G and BSA bound with different capture efficiencies to the binding medium 1620 in different concentrations of β-galactosidase (e.g., 0 µM, 0.2 µM, 0.8 µM, and 1.6 µM). Binding in 1 mM Immobiline is also shown for comparison. Material retention for both PG and BSA increased with increasing β-gal concentration up to 1.6 µM with PG reaching a maximum. Protein capture increased with increasing charge on oppositely charged surfaces. The lower capture efficiency of PG as compared to BSA may be due to PG having a lower Mr and surface charge. A weak interaction of BSA with the EBM was observed at 0 µM β-gal due to the PA gel having a negative charge. At higher concentrations of β-gal (e.g., 3.2 µM) in the EBM, protein capture was reduced (data not shown).

Figure 15B:
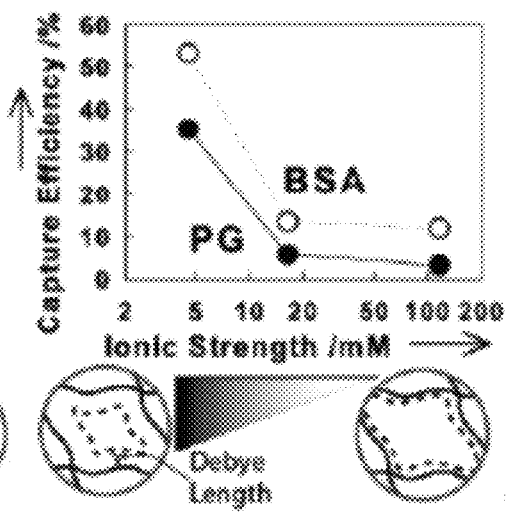
FIG. 15B shows a graph of capture efficiency (%) vs. ionic strength of the transfer buffer (mM), according to embodiments of the present disclosure.
Figure 16:
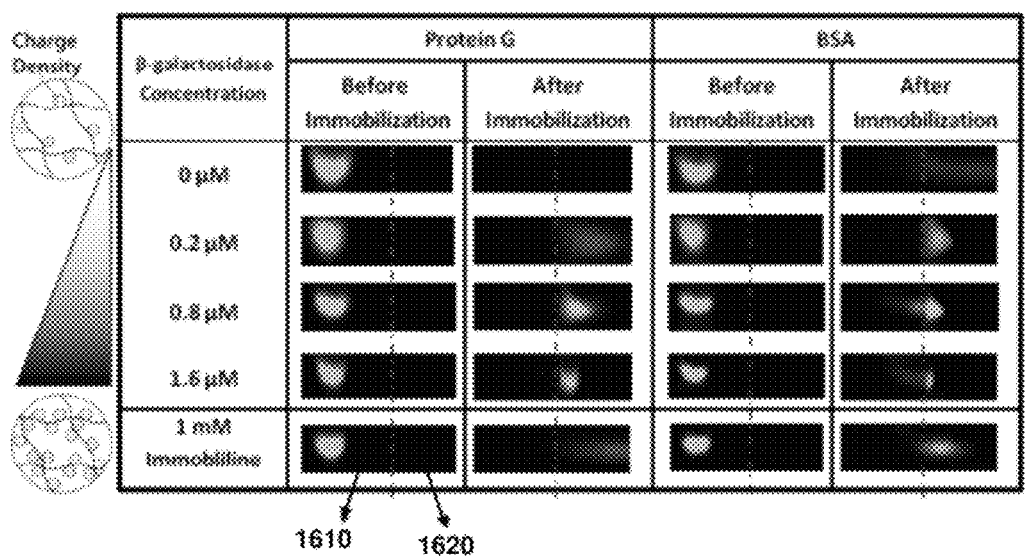
FIG. 16 shows fluorescence images of the binding strength of proteins in different charge densities and binding members (β-gal vs. Immobiline), according to embodiments of the present disclosure.
Figure 17:
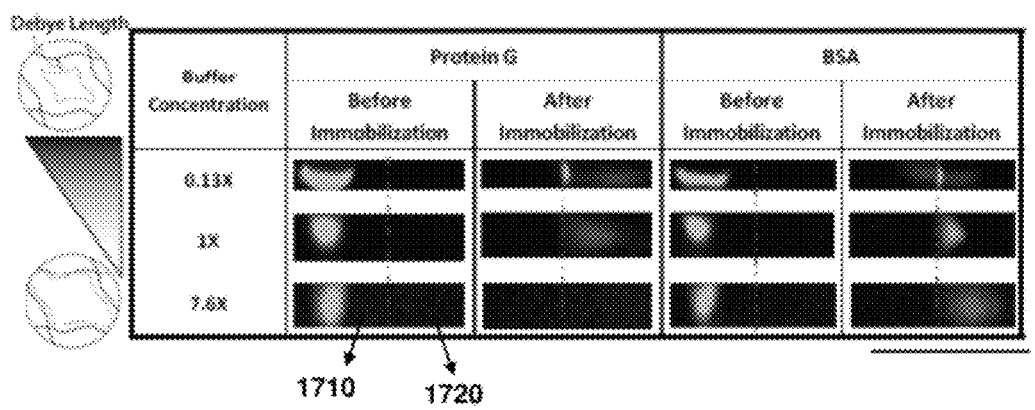
FIG. 17 shows fluorescence images of the binding strength of proteins in different ionic strength buffers (e.g., different buffer concentrations), according to embodiments of the present disclosure.

Experiments were performed in which the transfer-buffer ionic strength was varied to study the impact of Debye length in the EBM pores on protein capture (FIG. 15B). Three different ionic strength conditions were tested: 115.4 mM, 16.4 mM and 4.5 mM for 7.57×, 1× and 0.13×TA buffer+0.1% CTAB, respectively. As shown in FIG. 15B, protein capture decreased with increasing buffer ionic strength and enhanced charge shielding on the EBM. FIG. 17 shows fluorescence images of the binding strength of proteins in different ionic strength buffers (e.g., different buffer concentrations). Binding for protein G and BSA is shown to the separation medium 1710 and the electrostatic binding medium 1720 before and after binding (e.g., immobilization) to the binding medium in different buffer concentrations (e.g., 7.57×, 1× and 0.13×TA buffer+0.1% CTAB). As the Debye length decreased (e.g., increasing buffer ionic strength), protein capture efficiencies decreased due to an enhanced charge shielding effect.

Because CTAB association to proteins depended on buffer ionic strength, surface charge of the protein-CTAB complex also varied depending on ionic strength. In order to decouple this effect of varying surface charge to the protein capture from varying ionic strength, surface charge densities of protein G and BSA were characterized. As relative increase or decrease of surface charge $Q_S(C)$ at arbitrary buffer concentration C is of interest, $Q_S(C)/Q_S(C_0)$, relative charge density of CTAB-protein complexes relative to a standard concentration $C_0$ (1×TA buffer) was obtained. Henry's equation for electrophoretic mobility, electrophoretic mobility data, and hydrodynamic parameters of proteins were used in the calculation of $Q_S(C)/Q_S(C_0)$. A protein was assumed to be a perfect sphere (r=hydrodynamic radius) and to have evenly-distributed surface charges. 10×TA buffer was successively diluted to prepare 7.57×, 1×, and 0.13×TA buffer solutions, and 0.1% w/v CTAB was added to each buffer. Ionic strength was calculated as 115.4 mM, 16.37 mM, and 4.52 mM respectively. Fluorescently labeled PG (605 nM) and BSA (179 nM) was solubilized together in each buffer condition. Two proteins were separated in a double-T junction chip (Caliper Life Sciences) with uniform 6% T PA gel under a constant electric field. Electrophoretic mobility was obtained based on the speed of migration (i.e., time to travel a 2 mm distance in a straight microfluidic channel). The ratio of mobilities at different ionic strengths was calculated using a mathematical relationship between the free solution mobility and % T value (e.g., 6% T). The % T term was cancelled and then $Q_S(C)/Q_S(C_0)$ was expressed as a function of free solution mobility. Viscosity of the tricine-arginine buffer system was measured using a rotating rheometer (Physica MCR 301, Anton-Paar, Ashland, Va.). Stokes radius of BSA was obtained from literature. For the engineered recombinant PG (Invitrogen, 20 kDa), the radius was estimated from Stokes radii of proteins with similar Mr values. Finally, the relative negative surface charge at 7.57× and 0.13×TA buffer, with respect to 1×TA buffer, was calculated using Henry's description. Table 7 lists parameters used in the calculation, viscosity µ, experimentally obtained mobility at 6% T gel η, ratio between hydrodynamic radius of proteins a and Debye length $\lambda_D$, and surface charge ratio $Q_S(C)/Q_S(C_0)$.

indicated that electrostatic interaction was the dominant mechanism for protein capture on the EBM.

Example 6

Protein capture efficiency may be adjusted d by increasing the charge density and/or the decreasing buffer concentration. Additional experiments were performed to copolymerize a negatively charged binding member in the EBM. The negatively charged binding member used was an acrylamido buffer, an acidic Immobiline species (pK=3.8). Protein immobilization was observed using the Immobiline as the binding member.

Figure 18:
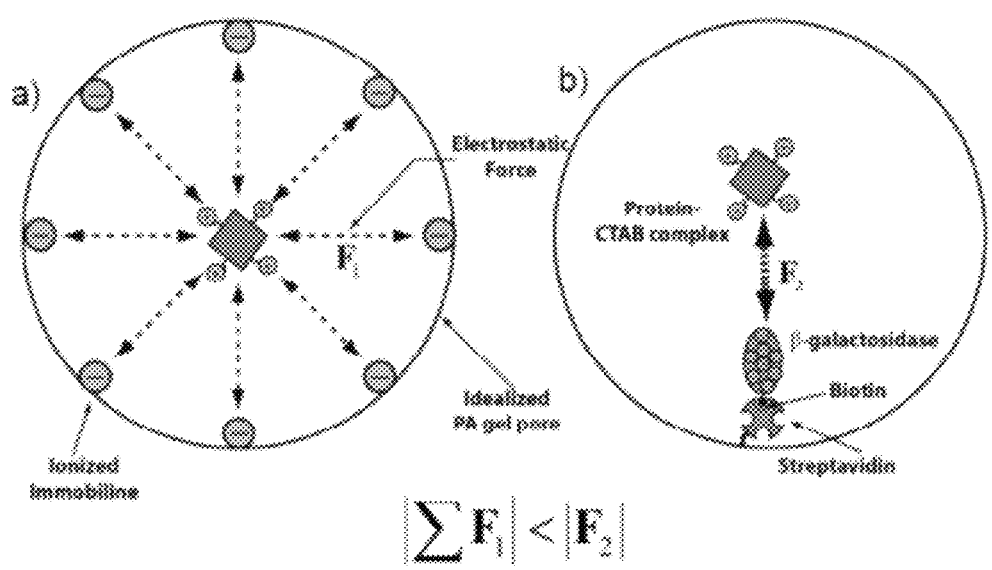
FIG. 18 shows schematics of a comparison of charge interaction between a CTAB-protein complex and a) Immobilines, and b) β-gal copolymerized in a polyacrylamide gel pore, according to embodiments of the present disclosure.

Experiments that included Immobiline in the electrostatic binding medium (EBM) were performed as follows. An acidic Immobiline species (pK=3.8, GE healthcare, Pittsburgh, Pa.) was copolymerized with the EBM. The EBM was fabricated with several different gel porosities (e.g., 6-10% T) and Immobiline concentrations (e.g., 0.1-10 mM), and capture efficiency was tested. Concentration polarization was observed at the EBM during the separation step (E=87 V/cm) for the highest concentration Immobiline used (10 mM). With this EBM, the current from control channel #5 (see FIG. 1B) decreased exponentially to less than 10% of the initial value after a few seconds. The decrease in current may be due to high stationary charge densities created at the interface between the separation medium and the electrostatic binding medium. At 1 mM Immobiline, moderate concentration polarization was observed, and CTAB-protein complexes were sized and immobilized on the EBM. The capture efficiency at this Immobiline concentration was calculated to be similar to that of the 0.2 µM β-gal copolymerized EBM, and was less than the capture efficiency using 1.6 µM of β-gal. The net charge density for 0.2 µM β-gal in the EBM was estimated to be 0.032 mM. At 0.1 mM Immobiline concentration, the protein capture on the EBM was equivalent to the baseline response of the 0 µM β-gal copolymerized EBM. FIG. 18 shows schematics of a comparison of charge interaction between a CTAB-protein complex and a) Immobilines, and b) β-gal copolymerized in a polyacrylamide gel pore. The pore geometry was idealized and Immobiline was assumed to be evenly distributed. Based on dimensional analysis, one to two molecules of β-gal were immobilized in each pore of a 6% T PA gel at 1.6 µM β-gal. β-gal molecules acted as a concentrated point charge (e.g., −160 per molecule). Charges originating from grafted Immobilines may be evenly distributed around each pore (FIG. 18). Thus, electrostatic attraction forces for Immobilines were in all directions, resulting in a vector force summation that may be less than the attraction towards point charges, such as β-gal.

TABLE 7

Hydrodynamic property and surface charge ratios of CTAB-PG and CTAB-BSA complexes in three different buffer concentrations

| Buffer Concentration | µ (mPa·s) | Protein G | | | BSA | | |
|---|---|---|---|---|---|---|---|
| | | η ($10^{-5} cm^2 s^{-1} V^{-1}$) | $a/\lambda_D$ | $Q_S(C)/Q_S(C_0)$ | η ($10^{-5} cm^2 s^{-1} V^{-1}$) | $a/\lambda_D$ | $Q_S(C)/Q_S(C_0)$ |
| 7.57x | 1.087 | 9.46 | 2.91 | 2.291 | 6.26 | 4.01 | 1.279 |
| 1x | 0.956 | 8.28 | 1.09 | 1 | 5.56 | 1.51 | 1 |
| 0.13x | 0.911 | 6.66 | 0.57 | 0.647 | 4.68 | 0.79 | 0.647 |

FIG. 15B indicates that protein capture decreased with increasing ionic strength, which was the opposite effect observed due to surface charge on protein capture. The decrease in protein capture with increasing ionic strength Example 7

Figure 19:
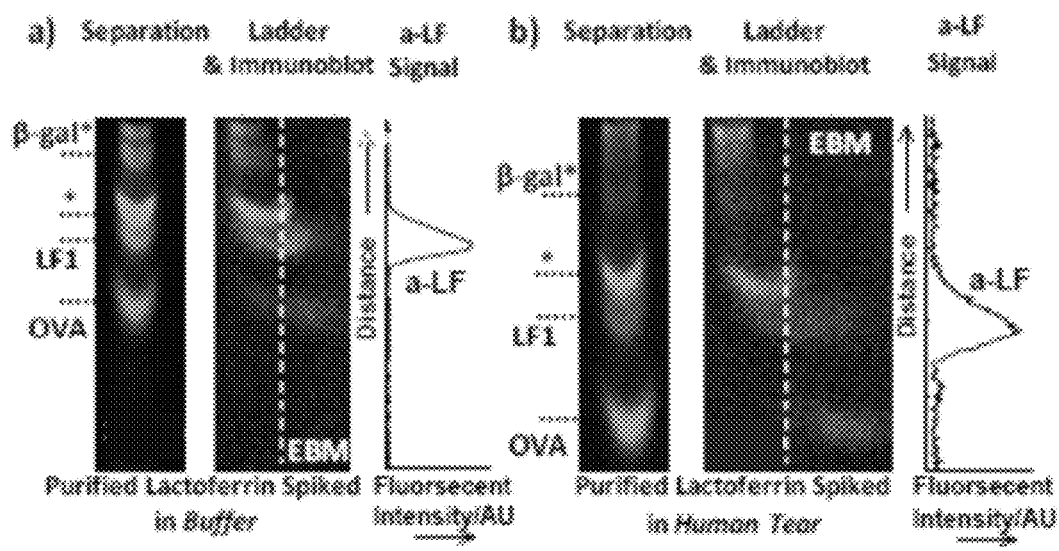
FIG. 19 shows fluorescence images of CTAB-PAGE separation and immunoblotting of a sample of proteins and human lactoferrin in: (a) 1×TA buffer and (b) human tear fluid, according to embodiments of the present disclosure.

Immunoblotting assays were performed to study protein biomarkers of disease and dysfunction. A microfluidic assay was performed for the analysis of lactoferrin (LF). LF is a biomarker for Sjögren's Syndrome, an autoimmune disease where immune cells attack exocrine glands. Microfluidic CTAB-PAGE analysis of LF in human tear fluid was performed. An increased CTAB concentration (0.5%) was used to prime the separation axis. Higher CTAB concentrations may increase shielding of negative charges on the PA separation gel, as LF was observed to non-specifically associate with the negatively charged separation medium. After an antibody screening, carrier-free anti-LF goat polyclonal antibody was used to produce a detectable signal for LF. Diluted BSA (0.2%) was used as the blocking buffer. FIG. 19(a) shows the results for a sample of LF purified from human breast milk (400 nM) spiked into 1×TA buffer+0.2% CTAB along with a protein ladder (OVA and β-gal*). At 16 s elapsed separation time (E=84 V/cm), CTAB-PAGE separated LF from the OVA and β-gal* (SR>1.5). An unresolved peak (*) about 85 kDa migrated closely with the LF peak. A control experiment showed the source of the unidentified peak as the β-gal* sample. Total separation time was 19 s and the total assay time, including antibody binding and detection, was 115 min. After binding to the binding medium, the detectable label antibody bound to LF (SNR=275, 5 min after starting the antibody wash step).

The assay was also performed on diluted tear fluid (48×) with 600 nM LF added (FIG. 19(b)). CTAB in the sample buffer was increased to 0.7% to facilitate detergent association due to the background of proteins in tear fluid (about 80 species, total 10 mg/mL). Fluorescence signal of a sample before separation was 31% of the signal for the case where no tear fluid matrix was included in the sample. At 14 s of elapsed separation time and 992 μm of separation length (E=60 V/cm), LF was separated from the co-migrating protein sample with the exception of the unidentified peak (*). Binding with antibody specific to LF was coincident with the LF band observed during CTAB-PAGE. SNR of the immunoblot to LF was 43 (5 min after starting the antibody wash step). Total separation time was 21 s and the total assay time, including antibody binding and detection, was 115 min.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A microfluidic device for detecting an analyte in a fluid sample, wherein the microfluidic device comprises a chamber containing a contiguous monolith comprising:
   a separation medium having a separation flow path with a first directional axis; and
   a pan-capture binding medium in fluid communication with the separation medium and having a flow path with a second directional axis,
   wherein the microfluidic device is configured to subject a sample to two or more directionally distinct flow fields coplanar with the separation medium.

2. The microfluidic device according to claim 1, wherein the binding medium is configured to non-specifically bind to analytes in the sample through electrostatic interactions.

3. The microfluidic device according to claim 1, wherein the binding medium is configured to have a negative charge.

4. The microfluidic device according to claim 3, wherein the binding medium comprises a negatively charged gel.

5. The microfluidic device according to claim 3, wherein the binding medium comprises a negatively charged pan-capture binding member stably associated with a support.

6. The microfluidic device according to claim 1, wherein the fluid sample comprises a detergent configured to provide analytes in the sample with a positive charge.

7. The microfluidic device according to claim 6, wherein the detergent comprises cetyltrimethylammonium bromide.

8. The microfluidic device according to claim 1, wherein the analyte comprises a fluorescent label.

9. The microfluidic device according to claim 1, wherein the two or more directionally distinct flow fields comprise two or more directionally distinct electric fields.

10. The microfluidic device according to claim 1, wherein the second directional axis orthogonal to the first directional axis.

11. The microfluidic device according to claim 1, wherein the microfluidic device comprises a chamber containing the separation medium and the binding medium.

12. The microfluidic device according to claim 1, wherein the contiguous monolith comprises a contiguous polymeric gel monolith.

13. The microfluidic device according to claim 1, wherein the contiguous monolith comprises a loading medium in fluid communication with the separation medium and having a flow path in the same direction as the first directional axis.

14. The microfluidic device according to claim 1, wherein the separation medium and the binding medium are in direct fluid communication with each other.

15. The microfluidic device according to claim 1, further comprising one or more microfluidic control channels configured to apply an electric field through the microfluidic device.

16. The microfluidic device according to claim 1, wherein the separation medium and the binding medium comprise a buffer.

17. The microfluidic device according to claim 16, wherein the microfluidic device does not include a sample or analyte.

18. A system for detecting an analyte in a fluid sample, the system comprising:
  (a) a microfluidic device configured to subject a sample to two or more directionally distinct flow fields coplanar with a separation medium, wherein the microfluidic device comprises a chamber containing a contiguous monolith comprising:
    (i) the separation medium having a separation flow path with a first directional axis; and
    (ii) a pan-capture binding medium in fluid communication with the separation medium and having a flow path with a second directional axis; and
  (b) a detector.

19. The microfluidic device according to claim 1, wherein the separation medium and the binding medium are configured such that the sample traverses directly from the separation medium to the binding medium.

20. The microfluidic device according to claim 4, wherein the binding medium comprises a negatively charged polyacrylamide gel.

21. The microfluidic device according to claim 5, wherein the binding member is a negatively charged protein or peptide.

22. The microfluidic device according to claim 5, wherein the binding member is selected from a group consisting of immunoglobulin-G, β-galactosidase and myosin, or combinations thereof.

23. The microfluidic device according to claim 20, wherein the polyacrylamide gel has a total acrylamide content ranging from 3% to 15%.

24. A method of detecting an analyte in a fluid sample, the method comprising:
  (a) introducing the fluid sample comprising the analyte into a microfluidic device configured to subject the sample to two or more directionally distinct flow fields coplanar with a separation medium, wherein the microfluidic device comprises a chamber containing a contiguous monolith comprising:
    (i) the separation medium having a separation flow path with a first directional axis; and
    (ii) a pan-capture binding medium in fluid communication with the separation medium and having a flow path with a second directional axis;
  (b) directing the sample through the separation medium to produce a separated sample; and
  (c) detecting the analyte in the separated sample.

25. The system according to claim 18, further comprising voltage shaping components configured to control the strength of an electric field applied to the microfluidic device.

26. The system according to claim 18, wherein the two or more directionally distinct flow fields comprise two or more directionally distinct electric fields.

27. The system according to claim 18, further comprising microfluidic components configured to direct a fluid through the microfluidic device.

28. A kit comprising:
  (a) a microfluidic device configured to subject a sample to two or more directionally distinct flow fields coplanar with a separation medium, wherein the microfluidic device comprises a chamber containing a contiguous monolith comprising:
    (i) the separation medium having a separation flow path with a first directional axis; and
    (ii) a pan-capture binding medium in fluid communication with the separation medium and having a flow path with a second directional axis; and
  (b) a buffer.

29. The kit according to claim 28, wherein the buffer comprises a detergent.

30. The kit according to claim 29, wherein the detergent comprises cetyltrimethylammonium bromide.

31. The kit according to claim 28, further comprising one or more reagents selected from the group consisting of a detection reagent, a release reagent, a detergent, a refolding reagent and a denaturing reagent.

32. The microfluidic device according to claim 1, wherein the separation medium is contiguously photopatterned side-by-side with the binding medium.

* * * * *